United States Patent [19]

Kawabata et al.

[11] Patent Number: 5,346,646
[45] Date of Patent: Sep. 13, 1994

[54] TETRALIN COMPOUND, LIQUID CRYSTAL MATERIAL, LIQUID CRYSTAL COMPOSITION AND LIQUID CRYSTAL ELEMENT

[75] Inventors: Junichi Kawabata; Hideo Yamaoka; Yuuichirou Tatsuki; Shinichi Nishiyama, all of Sodegaura, Japan

[73] Assignee: Mitsui Petrochemical Industries, Ltd., Tokyo, Japan

[21] Appl. No.: 45,682

[22] Filed: Apr. 14, 1993

[30] Foreign Application Priority Data

Apr. 14, 1992 [JP] Japan .................................. 4-94463

[51] Int. Cl.$^5$ .................. C09K 19/32; C07C 69/76
[52] U.S. Cl. .................. 252/299.62; 252/299.01; 560/56; 560/80
[58] Field of Search .................. 252/299.01, 299.61, 252/299.62, 299.63, 299.66, 299.67; 359/103; 560/56, 80

[56] References Cited

U.S. PATENT DOCUMENTS

| | | | |
|---|---|---|---|
| 4,391,731 | 7/1983 | Boller et al. | 252/299.62 |
| 4,613,209 | 9/1986 | Goodby et al. | 252/299.62 |
| 5,246,622 | 9/1993 | Shimizu et al. | 252/299.62 |

OTHER PUBLICATIONS

Liquid Crystal, Fundamental Editing, edited by Koji Okano and Shunsuke Kobayashi, published by Baihukan, p. 179, 1985.

Flussige Kristalle in Table No. II published by Grundstoffindustrie, pp. 319 and 320, 1984.

*Primary Examiner*—Robert L. Stoll
*Assistant Examiner*—Shean C. Wu
*Attorney, Agent, or Firm*—Sherman and Shalloway

[57] ABSTRACT

The present invention provides a tetralin compound represented by the following formula:

$$R-X-A^1-Y^1-A^2-(Y^2-A^3)_n-Z-R^*$$

wherein R is an alkyl group of 3–20 carbon atoms; X is —O—CO—, —O— or a single bond; n is 0 or 1; each of $A^1$, $A^2$ and $A^3$ is a divalent aromatic group; each of $Y^1$ and $Y^2$ is —COO—, —O—CO—, —CH$_2$CH$_2$—, —CH$_2$O— or —OCH$_2$—; Z is —O—, —O—CO— or a single bond; and R* is a specific optically active group.

The invention also provides a liquid crystal material comprising the above-mentioned tetralin compound, a liquid crystal composition comprising the tetralin compound and a liquid crystal compound other than the tetralin compound, and a liquid crystal element using the tetralin compound. The tetralin compound of the invention is favorably used as a liquid crystal material because it has a large tilt angle and shows excellent liquid crystal properties.

27 Claims, 10 Drawing Sheets

TETRALIN COMPOUND, LIQUID CRYSTAL MATERIAL, LIQUID CRYSTAL COMPOSITION AND LIQUID CRYSTAL ELEMENT

FIELD OF THE INVENTION

The present invention relates to a novel tetralin compound, a liquid crystal material comprising the tetralin compound, a liquid crystal composition comprising the tetralin compound and a liquid crystal compound other than the tetralin compound, and a liquid crystal element comprising the liquid crystal material.

BACKGROUND OF THE INVENTION

Display devices using liquid crystal compounds, which are used widely at present, are driven in a TN (twisted nematic) mode.

Such driving display devices, however, have problems that since the position of the molecule of the liquid crystal compound present in the element must be changed in order to change displayed images, the driving time necessary therefor is prolonged, and also a voltage necessary for changing the position of the molecule of the liquid crystal compound becomes higher and electric power consumption becomes larger.

Differing from switching elements utilizing the TN mode or a STN mode, switching elements comprising ferroelectric liquid crystal compounds are able to function as switching elements only by changing the direction of molecular orientation of the liquid crystal compounds, and hence the switching time required for operating the switching elements is prominently shortened. Further, because a Ps×E value obtained from a spontaneous polarization (Ps) of the ferroelectric liquid crystal compound and an intensity of the electric field (E) applied thereto is an effective energy output for changing the direction of molecular orientation of the liquid crystal compound, the electric power consumption required therefor can also be extremely reduced. Such ferroelectric liquid crystal compounds are suitable particularly for use in display devices for moving picture, because they have two stable states depending upon the direction of the applied electric field, namely, bi-stability, and have very favorable switching threshold value characteristics.

When such ferroelectric liquid crystal compounds are used in optical switching elements or the like, these compounds are required to have various characteristics such that an operating temperature is in the vicinity of or below ordinary temperature, an operating temperature range is broad, a switching speed is high (fast), and a switching threshold value voltage is within an appropriate range. In particular, of these characteristics, the operating temperature range is very important when the ferroelectric crystal compounds are put into practical use.

However, in ferroelectric liquid crystal compounds known hitherto, the operating temperature range is generally narrow, and even in the case of ferroelectric liquid crystal compounds having a wide operating temperature range, the operating temperature range is in a high temperature region out of room temperature, as described, for example, in a paper by R. B. Meyer et al., "J. de Phys.", Vol. 36, p. L-69 (1975) or in a paper by M. Taguchi and T. Harada, "Proceedings of Eleventh Conference on Liquid Crystal," p. 168 (1985). Thus, no ferroelectric liquid crystal compounds satisfactory from the standpoint of practical use are obtainable yet.

OBJECT OF THE INVENTION

An object of the present invention is to provide a novel tetralin compound, a liquid crystal material comprising the tetralin compound and a liquid crystal compound other than the tetralin compound, a liquid crystal composition comprising the tetralin compound and a liquid crystal element in which the tetralin compound is used. In particular, the object of the invention is to provide a novel tetralin compound capable of forming a liquid crystal element having excellent properties such as wide operating temperature range, high switching speed, prominently reduced electric power consumption and stable contrast, and uses of the tetralin compound.

SUMMARY OF THE INVENTION

The tetralin compound of the invention is represented by the following formula [I]:

$$R—X—A^1—Y^1—A^2—(Y^2—A^3)_n—Z—R^* \qquad [I]$$

wherein
R is an alkyl group of 3–20 carbon atoms,
X is —O—CO—, —O— or a single bond,
n is 0 or 1, and
when n is 0, one of $A^1$ and $A^2$ is

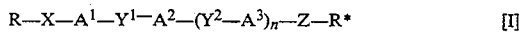

and the residual $A^1$ or $A^2$ is a group selected from the group consisting of

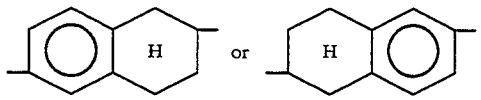

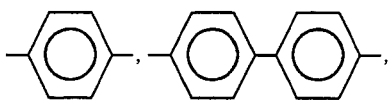

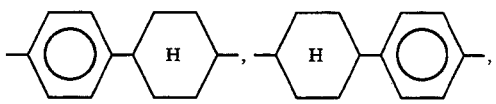

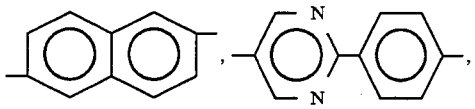

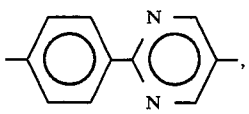

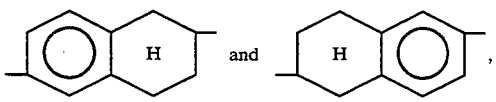

and when n is 1, one of $A^1$, $A^2$ and $A^3$ is

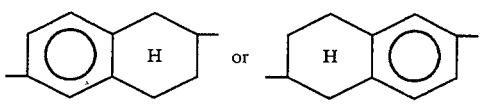

and the residual two of $A^1$ $A^2$ and $A^3$ are 1,4-phenylene group, $Y^1$ and $Y^2$ are each independently a group selected from the group consisting of —COO—, —O—CO—, —CH$_2$CH$_2$—, —CH$_2$O— and —OCH$_2$—, Z is —O—, —O—CO— or a single bond, and R* is a group selected from the group consisting of —C*H(CF$_3$)—C$_6$H$_{13}$, —C*H (CH$_3$) —C$_6$H$_{13}$, —C*H (CH$_3$) —C$_5$H$_{11}$, —C*H (C$_2$H$_5$)—C$_5$H$_{11}$, —C*H (C$_2$H$_5$)—C$_6$H$_{13}$, —CH$_2$13 C*H (CH$_3$) —C*H (C$_2$H$_5$)—C$_6$H$_{13}$, —CH$_2$— C*H (CH$_3$) (CF$_3$)—CH$_2$—COO—C$_2$H$_5$.

The liquid crystal material of the invention comprises the tetralin compound represented by the above formula [I].

The liquid crystal composition of the invention comprises the tetralin compound represented by the above formula [I] and a liquid crystal compound other than the tetralin compound.

The liquid crystal element of the invention is a liquid crystal element comprising a cell and a liquid crystal material or composition, said cell comprising two substrates facing to each other and a gap formed by the substrates, said liquid crystal material or composition being filled in the gap of the cell, wherein the liquid crystal material or composition comprises the tetralin compound represented by the above formula [I].

According to the present invention, a novel tetralin compound is provided. The tetralin compound is very useful as a liquid crystal material. Therefore, a liquid crystal composition comprising this tetralin compound shows excellent liquid crystal characteristics, and further a liquid crystal element formed by filling a liquid crystal material or composition comprising this tetralin compound in a gap between two substrates also shows excellent liquid crystal characteristics.

By the use of the tetralin compound of the invention as a liquid crystal material, there can be obtained various kinds of devices having excellent characteristics such as wide operating temperature range, high switching speed, very small electric power consumption and stable high contrast.

Figure 1:
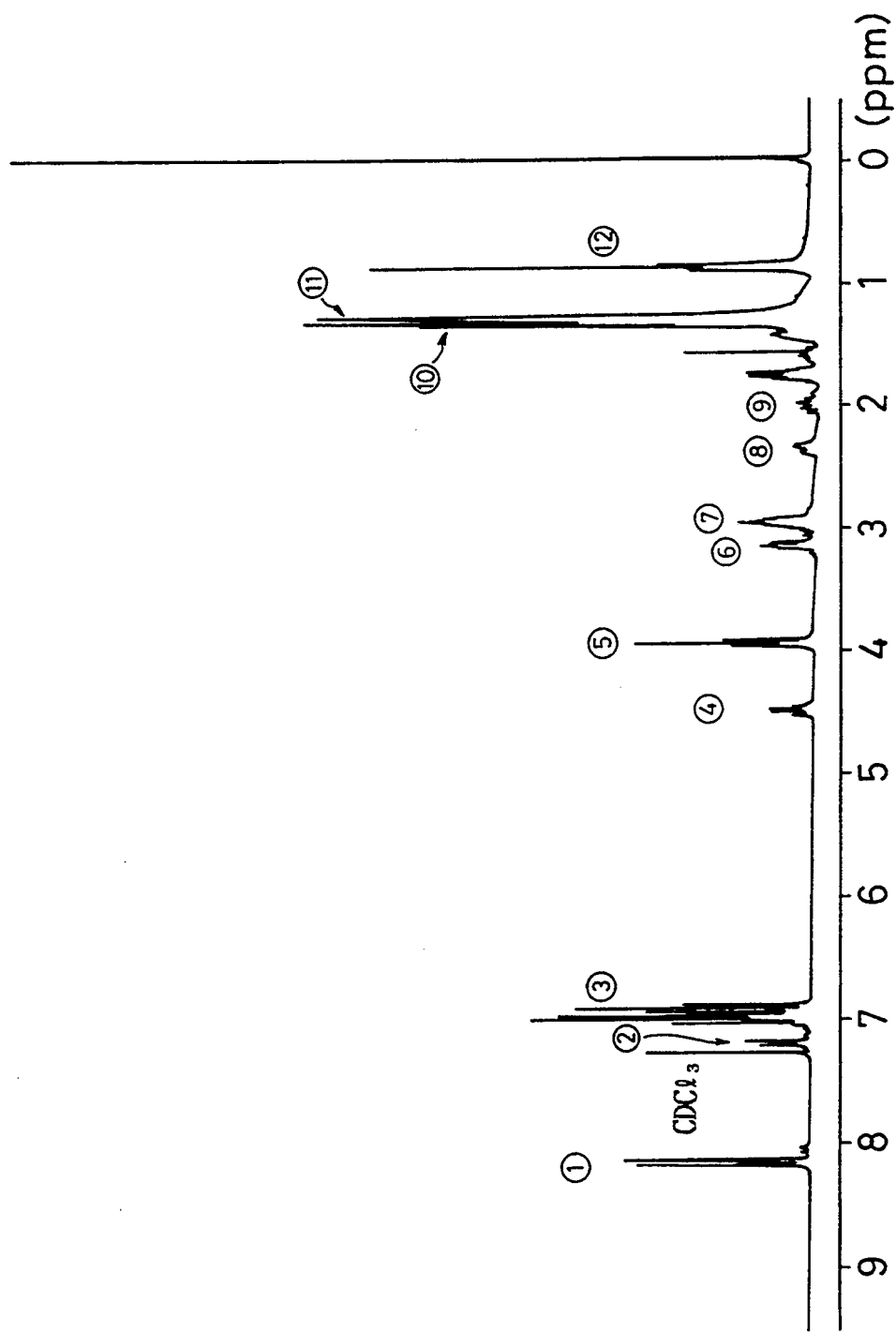
FIG. 1 shows a $^1$H-NMR spectrum of 6-[4'- (R-2''-octyloxy) benzoyloxy]-1,2,3,4-tetrahydronaphthalene-2-carboxylic acid-4'''-decyloxyphenyl ester [Exemplified Compound (4)].

11a, 11b, 27a, 27b, 37, 47, 57: transparent substrate
12, 23, 33, 43, 53: liquid crystal material
13, 58: cell
14: gap
15a, 15b, 25a, 25b, 35, 45, 55: transparent electrode
26: concentric spacer
36: comb-like spacer
46: fiber
56: polarizing plate

DETAILED DESCRIPTION ON THE INVENTIQN

The present invention is described below in detail.

First, the tetralin compound and the liquid crystal material of the invention are described.

The tetralin compound of the invention is represented by the following formula [I].

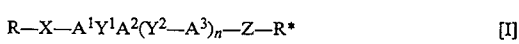

In the above formula [I], R is an alkyl group of 3-20 carbon atoms.

The liquid crystal material of the invention comprises the tetralin compound represented by the above formula [I].

The alkyl group may have any form of straight chain, branched and alicyclic forms. In particular, the tetralin compound having a straight chain alkyl group as R exhibits excellent liquid crystal properties because the molecule has a rigid linear structure. Concrete examples of the straight chain alkyl groups include hexyl group, heptyl group, octyl group, nonyl group, decyl group, undecyl group, dodecyl group, tetradecyl group, hexadecyl group and octadecyl group.

In the above formula [I], X is —O—CO—, —O— or a single bond. Of these, preferred is —O— or a single bond in view of characteristics of the tetralin compound used as a liquid crystal material.

In the above formula [I], n is 0 or 1. Accordingly, when n is 0, none of $Y^2$ and $A^3$ are present in the formula [I].

When n is 0, one of $A^1$ and $A^2$ is

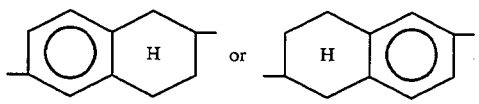

and the residual $A^1$ or $A^2$ is a group selected from the group consisting of

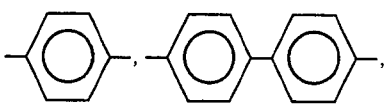

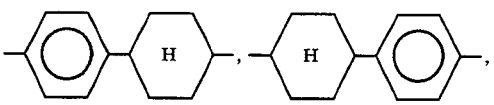

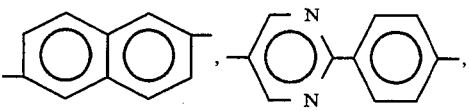

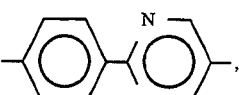

When n is 1, one of $A^1$, $A^2$ and $A^3$ is

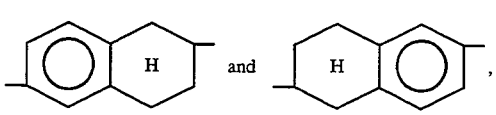

and the residual two of $A^1$ $A^2$ and $A^3$ are 1,4-phenylene group.

For the use of the tetralin compound of the invention as a liquid crystal compound, it is preferred that the molecule is linear as a whole. On that account, the 1,2,3,4-tetrahydronaphthyl group is preferably 1,2,3,4-tetrahydro-2,6-naphthyl group.

Likewise, the 5,6,7,8-tetrahydronaphthyl group is preferably 5,6,7,8-tetrahydro-2,6-naphthyl group.

Examples of structures of the tetralin compound represented by the formula [I] wherein $A^1$ $A^2$ and $A^3$ are the above-mentioned groups are given below. Examples of 1,2,3,4-tetrahydro-2,6-naphthyl group or 5,6,7,8-tetrahydro-2,6-naphthyl group are:

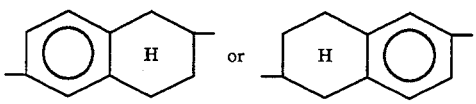

(1)

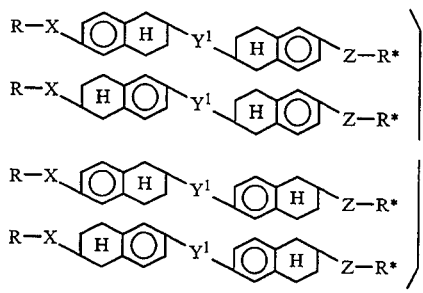

(2)

and

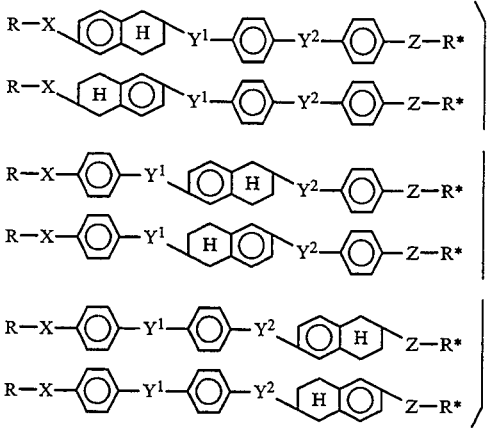

(3)

In the above examples, examples in the groups (1) and (2) are those of the tetralin compound represented by the formula [I] wherein n is 0, while examples in the groups (3) are those of the tetralin compound represented by the formula [I] wherein n is 1.

When n is 0, one of $A^1$ and $A^2$ is

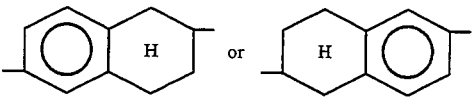

and the residual $A^1$ or $A^2$ is a group selected from the group consisting of

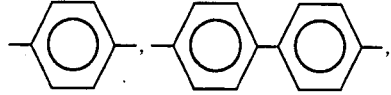

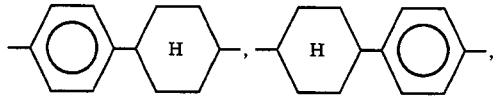

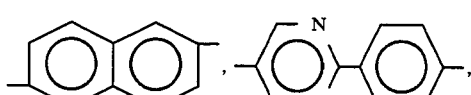

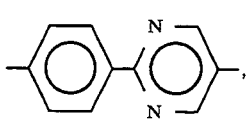

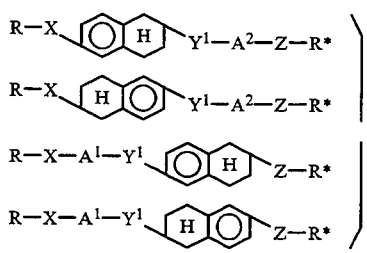

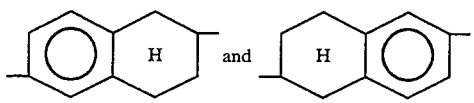

When n is 1, one of $A^1$ $A^2$ and $A^3$ is

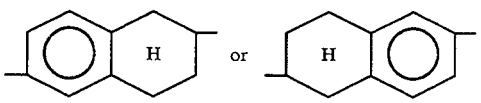

and the residual two of $A^1$, $A^2$ and $A^3$ are 1,4-phenylene group.

In the above formula [I], $Y^1$ and $Y^2$ are each independently a group selected from the group consisting of —COO—, —O—CO—, —CH₂CH₂—, —CH₂O— and —OCH₂—. When the tetralin compound of the invention is used as a liquid crystal material, it is preferred that $Y^1$ and $Y^2$ are each independently —COO—, —O—CO— or a single bond. Especially when the linearity of the molecule is taken into account, it is desirable that at least one of $Y^1$ and $Y^2$, preferably both of them, are —O—CO— or —COO—.

In the above formula [I], Z is —O—, —O—CO— or a single bond.

Particularly, a compound having —O— or —O—CO— as Z is prominently improved in the tilt angle, as compared with, for example, a compound having —COO— as Z.

The tilt angles of compounds represented by the following formula wherein Z is —O—, —O—CO— or —COO—, respectively, are shown in the following table.

As is apparent from the above table, the tilt angle of the tetralin compound is markedly changed by changing Z to —O—, —O—CO— or —COO—. The tetralin compound wherein Z is the group defined by the invention or a single bond has a large tilt angle, and particularly the tetralin compound wherein Z is —O— has an extremely large tilt angle. When such compound having a large tilt angle is used as a liquid crystal material, an optical switching element showing excellent properties can be obtained. Accordingly, for the use of the tetralin compound of the invention as a liquid crystal material, Z is particularly preferably —O—.

In the formula [I], R* is preferably a group selected from the group consisting of —C*H(CF₃) —C₆H₁₃, —C*H(CH₃)—C₆H₁₃, —C*H (CH₃) —C₅H₁₁, —C*H (C₂H₅)—C₅H₁₁, —C*H (C₂H₅)—C₆H₁₃,—CH₂—C*H(CH₃)—Ch₂H₅, —(CH₂)₃—C*H(CH₃)—C₂H₅ and —C*H(CF₃) —CH₂—COO—C₂H₅. That is, R* is an optically active group having at least one asymmetric carbon. A carbon atom which is bonded to the above-mentioned carbon atom for forming the optically active group may have a halogen atom such as a fluorine atom.

Of the above-mentioned groups, preferred is either of the following groups in view of characteristics of the tetralin compound used as a liquid crystal material.

—C*H(CF₃)—C₆H₁₃
—C*H(CH₃)—C₆H₁₃

Accordingly, concrete examples of the tetralin compound represented by the formula [I]are those set forth in Tables 1-1 to 1-3 and Tables 2-1 to 2-6.

That is, concrete examples of the tetralin compound represented by the formula [I] wherein n is 1, namely, a tetralin compound represented by the following formula [I-A], are shown in Table 1-1 to Table 1-3.

$$R-X-A^1-Y^1-A^2-Y^2-A^3-Z-R^* \quad [I-A]$$

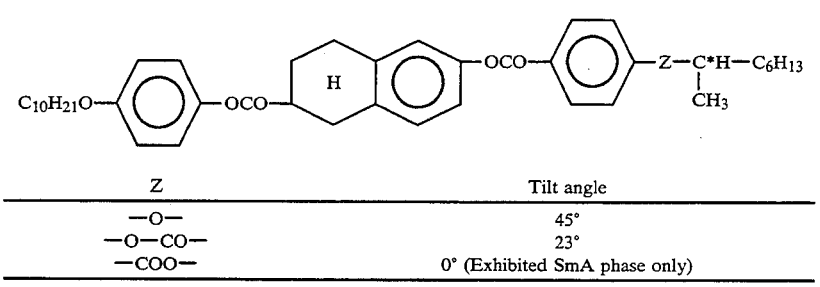

| Z | Tilt angle |
|---|---|
| —O— | 45° |
| —O—CO— | 23° |
| —COO— | 0° (Exhibited SmA phase only) |

TABLE 1-1

| [n = 1] Com. No. | R | X | $A^1$ | $Y^1$ | $A^2$ | Ex. No. |
|---|---|---|---|---|---|---|
| 1 | C₇H₁₅— | —O— | <phenylene> | —O—CO— | <tetralin H> | 1 |
| 2 | C₈H₁₇— | " | " | " | " | |
| 3 | C₉H₁₉— | " | " | " | " | |
| 4 | C₁₀H₂₁— | " | " | " | " | |
| 5 | C₁₁H₂₃— | " | " | " | " | |
| 6 | C₁₂H₂₃— | " | " | " | " | |
| 7 | C₁₄H₂₉— | " | " | " | " | |
| 8 | C₁₆H₃₃— | " | " | " | " | |

TABLE 1-1-continued
| Com. No. | R | X | A¹ | Y¹ | A² | |
|---|---|---|---|---|---|---|
| 9 | C7H15— | — | 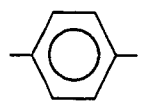 | —O—CO— | 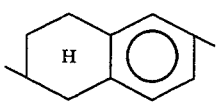 H | |
| 10 | C8H17— | " | " | " | " | |
| 11 | C9H19— | " | " | " | " | |
| 12 | C10H21— | " | " | " | " | |
| 13 | C11H23— | " | " | " | " | |
| 14 | C12H23— | " | " | " | " | |
| 15 | C14H29— | " | " | " | " | |
| 16 | C16H33— | " | " | " | " | |
| 17 | C7H15— | —O— | 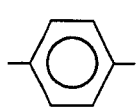 | O—CO— | 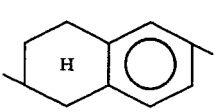 H | 5 |
| 18 | C8H17— | " | " | " | " | |
| 19 | C9H19— | " | " | " | " | |
| 20 | C10H21— | " | " | " | " | |
| 21 | C11H23— | " | " | " | " | |
| 22 | C12H23— | " | " | " | " | |
| 23 | C14H29— | " | " | " | " | |
| 24 | C16H33— | " | " | " | " | |
[n = 1]
| Com. No. | Y² | A³ | Z | R* | Ex. No. |
|---|---|---|---|---|---|
| 1 | —O—CO— |  | —O— | —C*H(CH3)C6H13 | 1 |
| 2 | " | " | " | " | |
| 3 | " | " | " | " | |
| 4 | " | " | " | " | |
| 5 | " | " | " | " | |
| 6 | " | " | " | " | |
| 7 | " | " | " | " | |
| 8 | " | " | " | " | |
| 9 | —O—CO— | 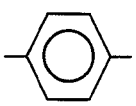 | —O— | —C*H(CH3)C6H13 | |
| 10 | " | " | " | " | |
| 11 | " | " | " | " | |
| 12 | " | " | " | " | |
| 13 | " | " | " | " | |
| 14 | " | " | " | " | |
| 15 | " | " | " | " | |
| 16 | " | " | " | " | |
| 17 | —O—CO— | 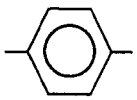 | —O—CO— | —C*H(CH3)C6H13 | 5 |
| 18 | " | " | " | " | |
| 19 | " | " | " | " | |
| 20 | " | " | " | " | |
| 21 | " | " | " | " | |
| 22 | " | " | " | " | |
| 23 | " | " | " | " | |
| 24 | " | " | " | " | |
TABLE 1-2
| Com. No. | R | X | A¹ | Y¹ | A² | Ex. No. |
|---|---|---|---|---|---|---|

TABLE 1-2-continued

| No. | R | X | A² | Y¹ | A³ (middle) |
|---|---|---|---|---|---|
| 25 | C₁₀H₂₁— | —O— | 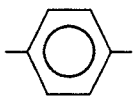 | —COO— | 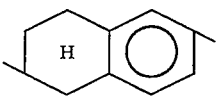 |
| 26 | " | " | " | —CH₂CH₂— | " |
| 27 | " | " | " | —CH₂O— | " |
| 28 | " | " | " | —OCH₂— | " |
| 29 | C₁₀H₂₁— | —O— | 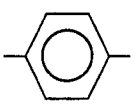 | —O—CO— | 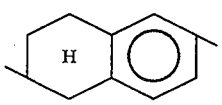 |
| 30 | " | " | " | " | " |
| 31 | " | " | " | " | " |
| 32 | " | " | " | " | " |
| 33 | " | " | " | " | " |
| 34 | " | " | " | " | " |
| 35 | C₁₀H₂₁— | —O— | 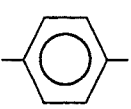 | —O—CO— | 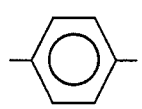 |
| 36 | C₁₀H₂₁— | — | " | " | " |
| 37 | C₁₀H₂₁— | —OCO— | " | " | " |
| 38 | C₁₀H₂₁— | —O— | 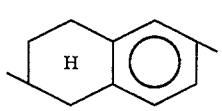 | —O—CO— | 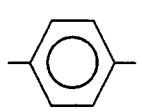 |
| 39 | C₁₀H₂₁— | — | " | " | " |
| 40 | C₁₀H₂₁— | —OCO— | " | " | " |
| 41 | C₁₀H₂₁— | —O— | 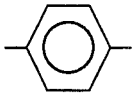 | —O—CO— | 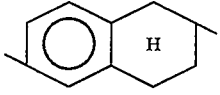 |
| 42 | C₁₀H₂₁— | — | " | " | " |
| 43 | C₁₀H₂₁— | —OCO— | " | " | " |

| Com. No. | Y² | A³ | Z | R* | Ex. No. |
|---|---|---|---|---|---|
| 25 | —O—CO— | 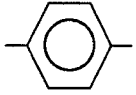 | —O— | —C*H(CH₃)C₆H₁₃ | |
| 26 | " | " | " | " | |
| 27 | " | " | " | " | |
| 28 | " | " | " | " | |
| 29 | —O—CO— | 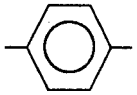 | —O— | —C*H(CF₃)C₅H₁₁ | |
| 30 | " | " | " | —C*H(C₂H₅)C₅H₁₁ | |
| 31 | " | " | " | —C*H(C₂H₅)C₆H₁₁ | |
| 32 | " | " | " | —CH₂—C*H(CH₃)—C₂H₅ | |
| 33 | " | " | " | —(CH₂)₃C*H(CH₃)—C₂H₅ | |
| 34 | " | " | " | —C*H(CF₃)CH₂—COO—C₂H₅ | |
| 35 | —O—CO— | 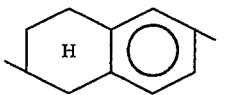 | —O— | —C*H(CH₃)C₆H₁₃ | |
| 36 | " | " | " | " | |
| 37 | " | " | " | " | |

TABLE 1-2-continued

| 38 | —O—CO— | 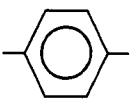 | —O— | —C*H(CH₃)C₆H₁₃ |
|----|---------|---|------|------------------|
| 39 | " | " | " | " |
| 40 | " | " | " | " |
| 41 | —O—CO— |  | —O— | —C*H(CH₃)C₆H₁₃ |
| 42 | " | " | " | " |
| 43 | " | " | " | " |

TABLE 1-3

| Com. No. | R | X | A¹ | Y¹ | A² | Ex. No. |
|----------|---|---|----|----|----|---------|
| 44 | C₁₀H₂₁— | —O— | 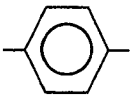 | —O—CO— | 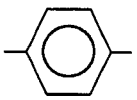 | |
| 45 | C₁₀H₂₁— | — | " | " | " | |
| 46 | C₁₀H₂₁— | —OCO— | " | " | " | |
| 47 | C₁₀H₂₁— | —O— | 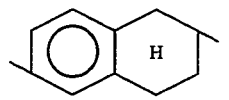 | —O—CO— | 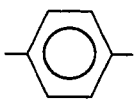 | |
| 48 | C₁₀H₂₁— | — | " | " | " | |
| 49 | C₁₀H₂₁— | —OCO— | " | " | " | |
| 50 | C₁₀H₂₁— | —O— | 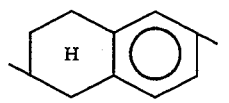 | —COO— | 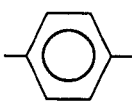 | 2 |
| 51 | C₁₀H₂₁— | — | " | " | " | |
| 52 | C₁₀H₂₁— | —OCO— | " | " | " | |

| Com. No. | Y² | A³ | Z | R* | Ex. No. |
|----------|----|----|---|-----|---------|
| 44 | —O—CO— | 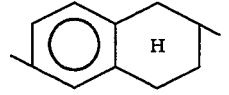 | —O— | —C*H(CH₃)C₆H₁₃ | |
| 45 | " | " | " | " | |
| 46 | " | " | " | " | |
| 47 | —O—CO— |  | —O— | —C*H(CH₃)C₆H₁₃ | |
| 48 | " | " | " | " | |
| 49 | " | " | " | " | |
| 50 | —COO— |  | —O— | —C*H(CH₃)C₆H₁₃ | 2 |
| 51 | " | " | " | " | |
| 52 | " | " | " | " | |

Further, concrete examples of the tetralin compound represented by the formula [I] wherein n is 0, namely, a tetralin compound represented by the following formula [I-B], are shown in Table 2-1 to Table 2-6.

R—X—A¹—Y¹—A²—Z—R*  [I-B]

TABLE 2-1

| [n = 0] Com. No. | R | X | A¹ | Y¹ | Ex. No. |
|---|---|---|---|---|---|
| 53 | C₁₀H₂₁— | —O— | naphthalene (H) | —O—CO— | |
| 54 | C₁₀H₂₁— | — | " | " | |
| 55 | C₉H₁₉— | —O—CO— | " | " | |
| 56 | C₁₀H₂₁— | —O— | naphthalene (H) | —O—CO— | |
| 57 | C₁₀H₂₁— | — | " | " | |
| 58 | C₉H₁₉— | —O—CO— | " | " | |
| 59 | C₁₀H₂₁— | —O— | naphthalene (H) | —O—CO— | |
| 60 | C₁₀H₂₁— | — | " | " | |
| 61 | C₉H₁₉— | —O—CO— | " | " | |
| 62 | C₁₀H₂₁— | —O— | naphthalene (H) | —O—CO— | |
| 63 | C₁₀H₂₁— | — | " | " | |
| 64 | C₉H₁₉— | —O—CO— | " | " | |
| 65 | C₁₀H₂₁— | —O— | naphthalene (H) | —O—CO— | |
| 66 | C₁₀H₂₁— | — | " | " | |
| 67 | C₉H₁₉— | —O—CO— | " | " | |
| 68 | C₁₀H₂₁— | —O— | naphthalene (H) | —O—CO— | |
| 69 | C₁₀H₂₁— | — | " | " | |
| 70 | C₉H₁₉— | —O—CO— | " | " | |

| Com. No. | A² | Z | R* | Ex. No. |
|---|---|---|---|---|
| 53 | phenyl | —O— | —C*H(CH₃)C₆H₁₃ | |
| 54 | " | " | " | |
| 55 | " | " | " | |
| 56 | biphenyl | —O— | —C*H(CH₃)C₆H₁₃ | |
| 57 | " | " | " | |
| 58 | " | " | " | |

TABLE 2-1-continued

| 59 | [phenyl-cyclohexyl] | —O— | —C*H(CH₃)C₆H₁₃ |
|---|---|---|---|
| 60 | " | " | " |
| 61 | " | " | " |
| 62 | [cyclohexyl-phenyl] | —O— | —C*H(CH₃)C₆H₁₃ |
| 63 | " | " | " |
| 64 | " | " | " |
| 65 | [naphthyl] | —O— | —C*H(CH₃)C₆H₁₃ |
| 66 | " | " | " |
| 67 | " | " | " |
| 68 | [pyrazine-phenyl] | —O— | —C*H(CH₃)C₆H₁₃ |
| 69 | " | " | " |
| 70 | " | " | " |

TABLE 2-2

| Com. No. | R | X | A¹ | Y¹ | Ex. No. |
|---|---|---|---|---|---|
| 71 | $C_{10}H_{21}$— | —O— | [cyclohexyl-phenyl fused] | —O—CO— | |
| 72 | $C_{10}H_{21}$— | — | " | " | |
| 73 | $C_{9}H_{19}$— | —O—CO— | " | " | |
| 74 | $C_{10}H_{21}$— | —O— | [cyclohexyl-phenyl fused] | —O—CO— | |
| 75 | $C_{10}H_{21}$— | — | " | " | |
| 76 | $C_{9}H_{19}$— | —O—CO— | " | " | |
| 77 | $C_{10}H_{21}$— | —O— | [phenyl-cyclohexyl fused] | —O—CO— | |
| 78 | $C_{10}H_{21}$— | — | " | " | |
| 79 | $C_{9}H_{19}$— | —O—CO— | " | " | |
| 80 | $C_{10}H_{21}$— | —O— | [phenyl-cyclohexyl fused] | —O—CO— | |
| 81 | $C_{10}H_{21}$— | — | " | " | |
| 82 | $C_{9}H_{19}$— | —O—CO— | " | " | |

TABLE 2-2-continued

| Com. No. | | | | |
|---|---|---|---|---|
| 83 | C$_{10}$H$_{21}$— | —O— | (2-naphthyl-H) | —O—CO— |
| 84 | C$_{10}$H$_{21}$— | — | " | " |
| 85 | C$_9$H$_{19}$— | —O—CO— | " | " |
| 86 | C$_{10}$H$_{21}$— | —O— | (2-naphthyl-H) | —O—CO— |
| 87 | C$_{10}$H$_{21}$— | — | " | " |
| 88 | C$_9$H$_{19}$— | —O—CO— | " | " |

| Com. No. | A$^2$ | Z | R* | Ex. No. |
|---|---|---|---|---|
| 71 | phenyl-pyrimidinyl | —O— | —C*H(CH$_3$)C$_6$H$_{13}$ | |
| 72 | " | " | " | |
| 73 | " | " | " | |
| 74 | naphthyl-H | —O— | —C*H(CH$_3$)C$_6$H$_{13}$ | |
| 75 | " | " | " | |
| 76 | " | " | " | |
| 77 | naphthyl-H | —O— | —C*H(CH$_3$)C$_6$H$_{13}$ | |
| 78 | " | " | " | |
| 79 | " | " | " | |
| 80 | phenyl | —O— | —C*H(CH$_3$)C$_6$H$_{13}$ | |
| 81 | " | " | " | |
| 82 | " | " | " | |
| 83 | biphenyl | —O— | —C*H(CH$_3$)C$_6$H$_{13}$ | |
| 84 | " | " | " | |
| 85 | " | " | " | |
| 86 | phenyl-cyclohexyl-H | —O— | —C*H(CH$_3$)C$_6$H$_{13}$ | |
| 87 | " | " | " | |
| 88 | " | " | " | |

TABLE 2-3

| Com. No. | R | X | A¹ | Y¹ | Ex. No. |
|---|---|---|---|---|---|
| 89 | $C_{10}H_{21}-$ | $-O-$ | trans-decalin (H) | $-O-CO-$ | |
| 90 | $C_{10}H_{21}-$ | — | " | " | |
| 91 | $C_9H_{19}-$ | $-O-CO-$ | " | " | |
| 92 | $C_{10}H_{21}-$ | $-O-$ | trans-decalin (H) | $-O-CO-$ | |
| 93 | $C_{10}H_{21}-$ | — | " | " | |
| 94 | $C_9H_{19}-$ | $-O-CO-$ | " | " | |
| 95 | $C_{10}H_{21}-$ | $-O-$ | trans-decalin (H) | $-O-CO-$ | |
| 96 | $C_{10}H_{21}-$ | — | " | " | |
| 97 | $C_9H_{19}-$ | $-O-CO-$ | " | " | |
| 98 | $C_{10}H_{21}-$ | $-O-$ | trans-decalin (H) | $-O-CO-$ | |
| 99 | $C_{10}H_{21}-$ | — | " | " | |
| 100 | $C_9H_{19}-$ | $-O-CO-$ | " | " | |
| 101 | $C_{10}H_{21}-$ | $-O-$ | trans-decalin (H) | $-O-CO-$ | |
| 102 | $C_{10}H_{21}-$ | — | " | " | |
| 103 | $C_9H_{19}-$ | $-O-CO-$ | " | " | |
| 104 | $C_{10}H_{21}-$ | $-O-$ | trans-decalin (H) | $-O-CO-$ | |
| 105 | $C_{10}H_{21}-$ | — | " | " | |
| 106 | $C_9H_{19}-$ | $-O-CO-$ | " | " | |

| Com. No. | A² | Z | R* | Ex. No. |
|---|---|---|---|---|
| 89 | cyclohexyl-phenyl (H) | $-O-$ | $-C^*H(CH_3)C_6H_{13}$ | |
| 90 | " | " | " | |
| 91 | " | " | " | |
| 92 | naphthyl | $-O-$ | $-C^*H(CH_3)C_6H_{13}$ | |
| 93 | " | " | " | |
| 94 | " | " | " | |

TABLE 2-3-continued
| | | | |
|---|---|---|---|
| 95 | 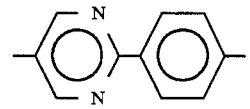 | —O— | —C*H(CH$_3$)C$_6$H$_{13}$ |
| 96 | " | " | " |
| 97 | " | " | " |
| 98 | 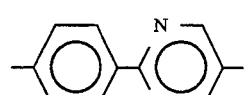 | —O— | —C*H(CH$_3$)C$_6$H$_{13}$ |
| 99 | " | " | " |
| 100 | " | " | " |
| 101 | 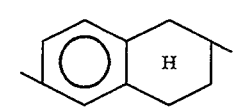 | —O— | —C*H(CH$_3$)C$_6$H$_{13}$ |
| 102 | " | " | " |
| 103 | " | " | " |
| 104 | 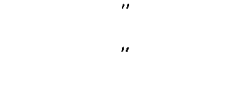 | —O— | —C*H(CH$_3$)C$_6$H$_{13}$ |
| 105 | " | " | " |
| 106 | " | " | " |
TABLE 2-4
| Com. No. | R | X | A$^1$ | Y$^1$ | Ex. No. |
|---|---|---|---|---|---|
| 107 | C$_{10}$H$_{21}$— | —O— |  | —O—CO— | |
| 108 | C$_{10}$H$_{21}$— | — | " | " | |
| 109 | C$_9$H$_{19}$— | —O—CO— | " | " | |
| 110 | C$_{10}$H$_{21}$— | —O— | 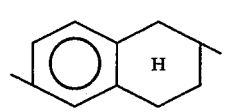 | —O—CO— | |
| 111 | C$_{10}$H$_{21}$— | — | " | " | |
| 112 | C$_9$H$_{19}$— | —O—CO— | " | " | |
| 113 | C$_{10}$H$_{21}$— | —O— |  | —O—CO— | |
| 114 | C$_{10}$H$_{21}$— | — | " | " | |
| 115 | C$_9$H$_{19}$— | —O—CO— | " | " | |
| 116 | C$_{10}$H$_{21}$— | —O— | 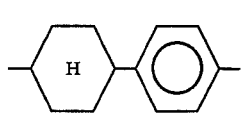 | —O—CO— | |
| 117 | C$_{10}$H$_{21}$— | — | " | " | |

TABLE 2-4-continued
| | | | | | |
|---|---|---|---|---|---|
| 118 | C9H19— | —O—CO— | " | " | |
| 119 | C10H21— | —O— | 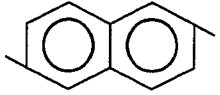 | —O—CO— | |
| 120 | C10H21— | — | " | " | |
| 121 | C9H19— | —O—CO— | " | " | |
| 122 | C10H21— | —O— | 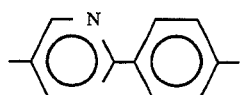 | —O—CO— | |
| 123 | C10H21— | — | " | " | |
| 124 | C9H19— | —O—CO— | " | " | |
| Com. No. | A² | Z | R* | Ex. No. |
|---|---|---|---|---|
| 107 | 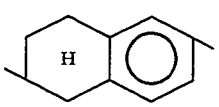 | —O— | —C*H(CH3)C6H13 | |
| 108 | " | " | " | |
| 109 | " | " | " | |
| 110 | 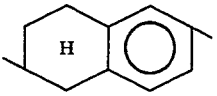 | —O— | —C*H(CH3)C6H13 | |
| 111 | " | " | " | |
| 112 | " | " | " | |
| 113 | 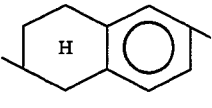 | —O— | —C*H(CH3)C6H13 | |
| 114 | " | " | " | |
| 115 | " | " | " | |
| 116 | 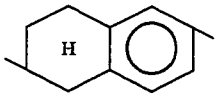 | —O— | —C*H(CH3)C6H13 | |
| 117 | " | " | " | |
| 118 | " | " | " | |
| 119 | 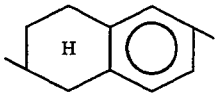 | —O— | —C*H(CH3)C6H13 | |
| 120 | " | " | " | |
| 121 | " | " | " | |
| 122 | 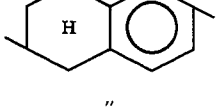 | —O— | —C*H(CH3)C6H13 | |
| 123 | " | " | " | |

TABLE 2-4-continued
| 124 | " | " | " |
|---|---|---|---|
TABLE 2-5
| Com. No. | R | X | A¹ | Y¹ | Ex. No. |
|---|---|---|---|---|---|
| 125 | $C_{10}H_{21}-$ | —O— | 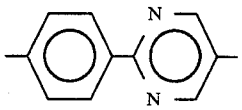 | —O—CO— | |
| 126 | $C_{10}H_{21}-$ | — | " | " | |
| 127 | $C_9H_{19}-$ | —O—CO— | " | " | |
| 128 | $C_{10}H_{21}-$ | —O— | 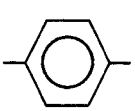 | —O—CO— | |
| 129 | $C_{10}H_{21}-$ | — | " | " | |
| 130 | $C_9H_{19}-$ | —O—CO— | " | " | |
| 131 | $C_{10}H_{21}-$ | —O— |  | —O—CO— | |
| 132 | $C_{10}H_{21}-$ | — | " | " | |
| 133 | $C_9H_{19}-$ | —O—CO— | " | " | |
| 134 | $C_{10}H_{21}-$ | —O— | 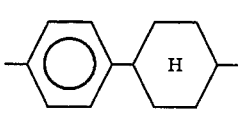 | —O—CO— | |
| 135 | $C_{10}H_{21}-$ | — | " | " | |
| 136 | $C_9H_{19}-$ | —O—CO— | " | " | |
| 137 | $C_{10}H_{21}-$ | —O— | 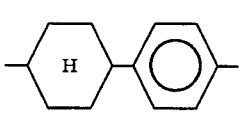 | —O—CO— | |
| 138 | $C_{10}H_{21}-$ | — | " | " | |
| 139 | $C_9H_{19}-$ | —O—CO— | " | " | |
| 140 | $C_{10}H_{21}-$ | —O— | 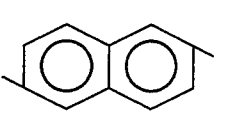 | —O—CO— | |
| 141 | $C_{10}H_{21}-$ | — | " | " | |
| 142 | $C_9H_{19}-$ | —O—CO— | " | " | |
| Com. No. | A² | Z | R* | Ex. No. |
|---|---|---|---|---|
| 125 | 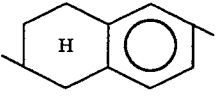 | —O— | —C*H(CH₃)C₆H₁₃ | |
| 126 | " | " | " | |
| 127 | " | " | " | |
| 128 | 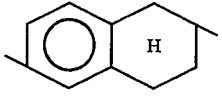 | —O— | —C*H(CH₃)C₆H₁₃ | |

TABLE 2-5-continued

| | | | |
|---|---|---|---|
| 129 | " | " | " |
| 130 | " | " | " |
| 131 | naphthalene-H | —O— | —C*H(CH₃)C₆H₁₃ |
| 132 | " | " | " |
| 133 | " | " | " |
| 134 | naphthalene-H | —O— | —C*H(CH₃)C₆H₁₃ |
| 135 | " | " | " |
| 136 | " | " | " |
| 137 | naphthalene-H | —O— | —C*H(CH₃)C₆H₁₃ |
| 138 | " | " | " |
| 139 | " | " | " |
| 140 | naphthalene-H | —O— | —C*H(CH₃)C₆H₁₃ |
| 141 | " | " | " |
| 142 | " | " | " |

TABLE 2-6

| Com. No. | R | X | A¹ | Y¹ | Ex. No. |
|---|---|---|---|---|---|
| 143 | C₁₀H₂₁— | —O— | pyrimidine-phenyl | —O—CO— | |
| 144 | C₁₀H₂₁— | — | " | " | |
| 145 | C₉H₁₉— | —O—CO— | " | " | |
| 146 | C₁₀H₂₁— | —O— | phenyl-pyrimidine | —O—CO— | |
| 147 | C₁₀H₂₁— | — | " | " | |
| 148 | C₉H₁₉— | —O—CO— | " | " | |
| 149 | C₁₀H₂₁— | —O— | naphthalene-H | —COO— | 3 |
| 150 | C₁₀H₂₁— | — | " | " | |
| 151 | C₉H₁₉— | —O—CO— | " | " | |

| Com. No. | A² | Z | R* | Ex. No. |
|---|---|---|---|---|

TABLE 2-6-continued
| 143 | (tetralin structure) | —O— | —C*H(CH₃)C₆H₁₃ | |
| --- | --- | --- | --- | --- |
| 144 | " | " | " | |
| 145 | " | " | " | |
| 146 | (tetralin structure) | —O— | —C*H(CH₃)C₆H₁₃ | |
| 147 | " | " | " | |
| 148 | " | " | " | |
| 149 | (phenylene) | —O— | —C*H(CH₃)C₆H₁₃ | 3 |
| 150 | " | " | " | |
| 151 | " | " | " | |
Such tetralin compound as described above can be prepared by means of a combination of known synthetic techniques.
For example, the tetralin compound can be synthesized in accordance with the following synthesis route.
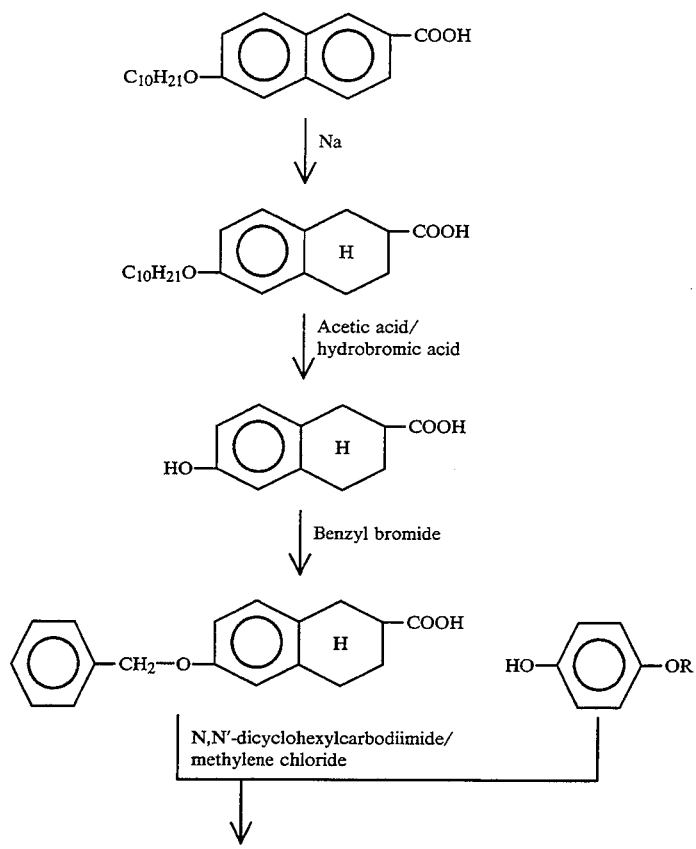

-continued

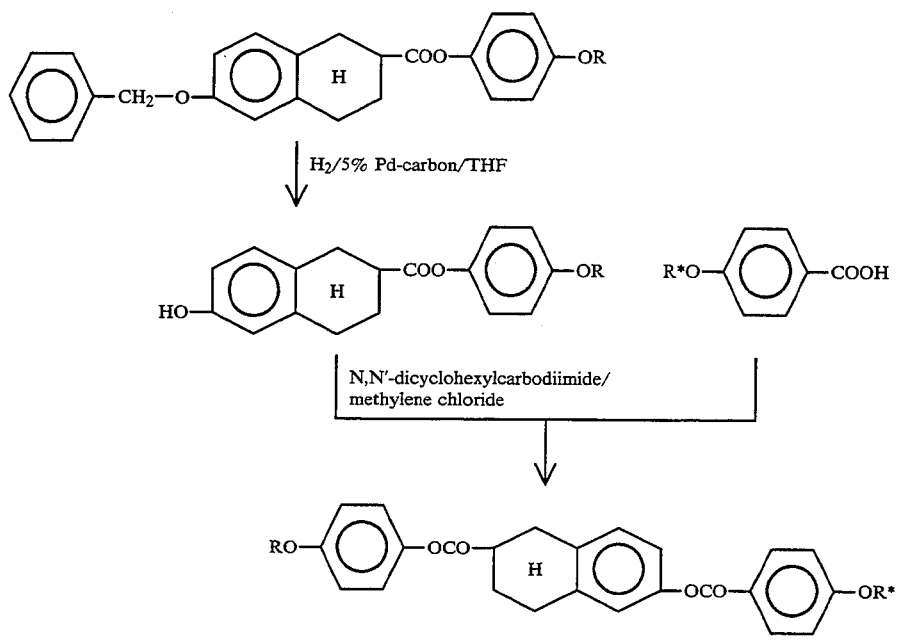

That is, for example, a mixture of 6-alkoxynaphthalene-2-carboxylic acid and 1,2-diethoxyethane is refluxed while dropwise adding isoamyl alcohol to the mixture in the presence of metallic sodium, to obtain 1,2,3,4-tetrahydro-6-alkoxynaphthalene-2-carboxylic acid.

The 1,2,3,4-tetrahydro-6-alkoxynaphthalene-2-carboxylic acid thus obtained is reacted with acetic acid and hydrobromic acid, to obtain 1,2,3,4-tetrahydro-6-hydroxynaphthalene-2-carboxylic acid.

The 1,2,3,4-tetrahydro-6-hydroxynaphthalene-2-carboxylic acid thus obtained is reacted with benzyl bromide in the presence of potassium hydroxide, to obtain 1,2,3,4-tetrahydro-6-benzyloxynaphthalene-2-carboxylic acid.

Subsequently, hydroquinone monoalcohol ether separately synthesized by a conventional process is reacted with the 1,2,3,4-tetrahydro-6-benzyloxynaphthalene-2-carboxylic acid obtained in the above step in the presence of 4-N,N-dimethylaminopyridine and methylene chloride (as a solvent) while dropwise adding a solution of N,N'-dicyclohexylcarbodiimide, to obtain 1,2,3,4-tetrahydro-6-benzyloxynaphthalene-2-carboxylic acid-4'-alkoxyphenyl ester.

The 1,2,3, 4-tetrahydro-6-benzyloxynaphthalene-2-carboxylic acid-4'-alkoxyphenyl ester thus obtained is introduced into a solvent such as tetrahydrofuran, and the resulting solution is reduced with hydrogen in the presence of a reducing catalyst such as palladium/carbon, to obtain 1,2,3,4-tetrahydro-6-hydroxynaphthalene-2-carboxylic acid-4'-alkoxyphenyl ester.

Then, 4-alkoxybenzoic acid containing an asymmetric carbon is reacted with the 1,2,3,4-tetrahydro-6-hydroxynaphthalene-2-carboxylic acid-4'-alkoxyphenyl ester obtained in the above step in the presence of 4-N,N-dimethylaminopyridine and methylene chloride (as a solvent) while dropwise adding a solution of N,N'-dicyclohexylcarbodiimide, to obtain the tetralin compound of the invention.

The above-described process is one example of a process for preparing the tetralin compound of the invention, and the tetralin compound of the invention is in no way limited to the compound prepared by the process.

A $^1$H-NMR spectrum of 6-[4'-(R-2''-octyloxy)benzoyloxy]-1,2,3,4-tetrahydronaphthalene-2-carboxylic acid-4'''-decyloxyphenyl ester [Exemplified Compound (4)]represented by the following formula, which is one example of the tetralin compound of the invention, is shown in FIG. 1.

In the following formula, symbols "eq" and "ax" mean equatorial conformation and axial conformation, respectively.

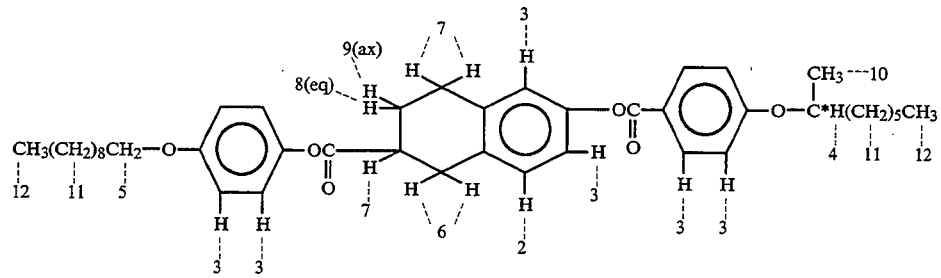

Figure 2:
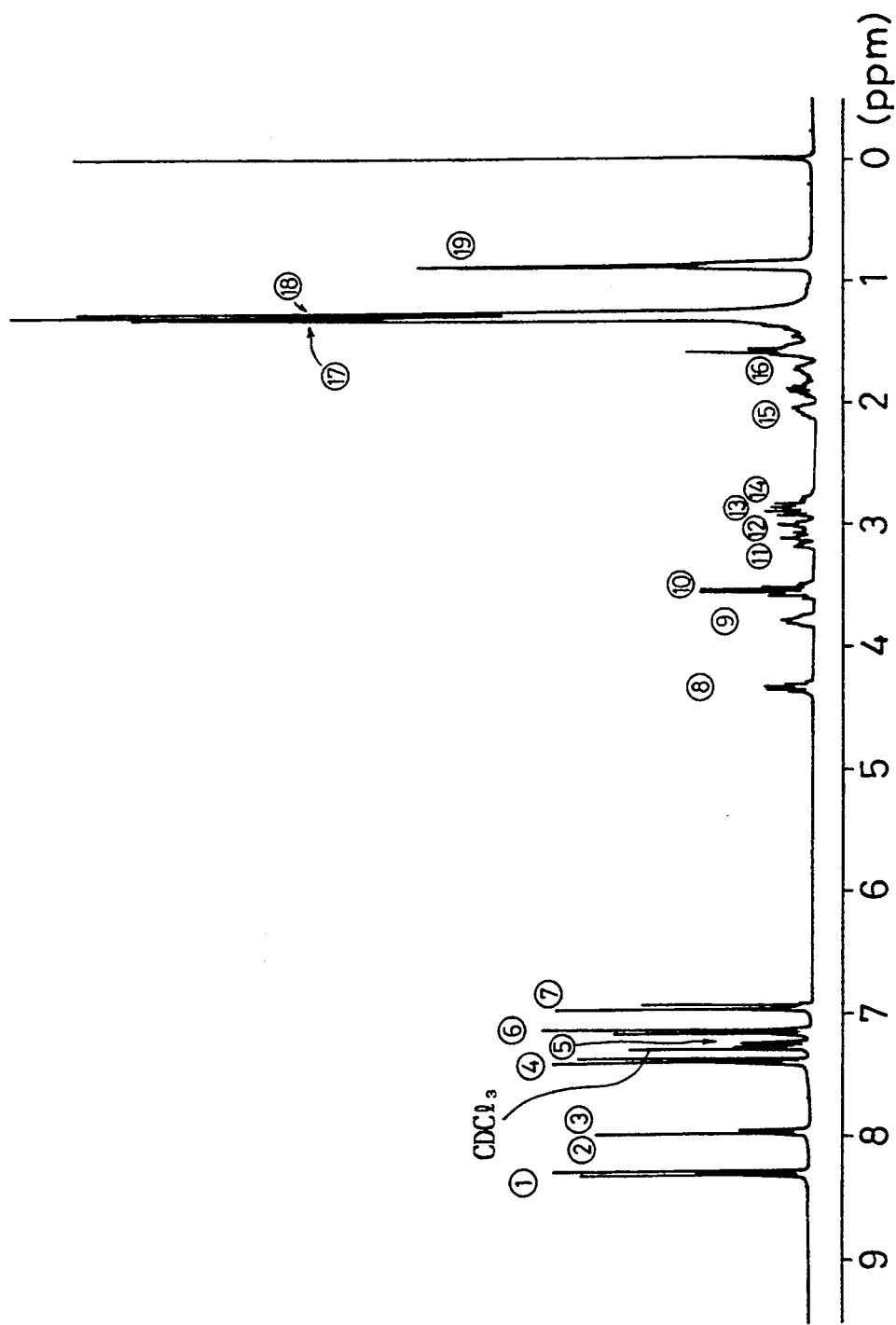
FIG. 2 shows a 1H-NMR spectrum of 4-(6'-decyloxy-5', 6', 7', 8'-tetrahydro-2''-naphthoyloxy)benzoic acid-4''-(R-2'''-octyloxy)phenyl ester [Exemplified Compound (50)].

In the above formula, each of numbers 1 to 12 indicates hydrogen atom, and each of the numbers corresponds to the same number attached to either one of peaks shown in FIG. 1. A $^1$H-NMR spectrum of 4-(6'- decyloxy-5′, 6′, 7′, 8′-tetrahydro-2″-naphthoyloxy) benzoic acid-4″- (R-2′″-octyloxy)phenyl ester [Exemplified Compound (50) ] represented by the following formula, which is also one example of the tetralin compound of the invention, is shown in FIG. 2.

The tetralin compound of the formula [I] obtained as above may be used, for example, as a liquid crystal material.

In particular, the tetralin compound having optical activity may be used as a ferroelectric liquid crystal

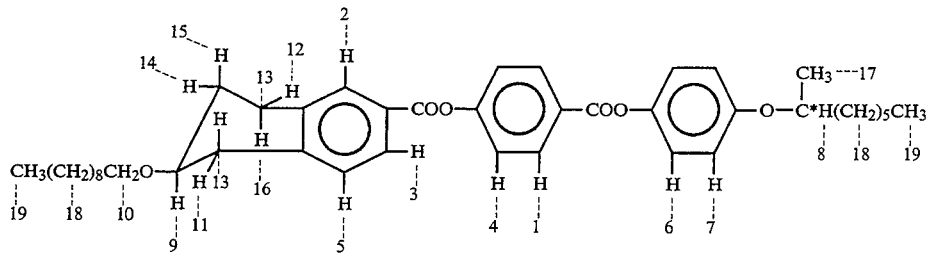

In the above formula, each of numbers 1 to 19 indicates hydrogen atom, and each of the numbers corresponds to the same number attached to either one of 20 peaks shown in FIG. 2.

A $^1$H-NMR spectrum of 6-decyloxy-1,2,3,4-tetrahydronaphthalene-2-carboxylic acid-4′- (R-2″-octyloxy)- compound or an antiferroelectric liquid crystal compound.

Of such tetralin compounds as described above, compounds represented by the following formulas [4], [20], 50] and [149] exhibit particularly excellent liquid crystal characteristics.

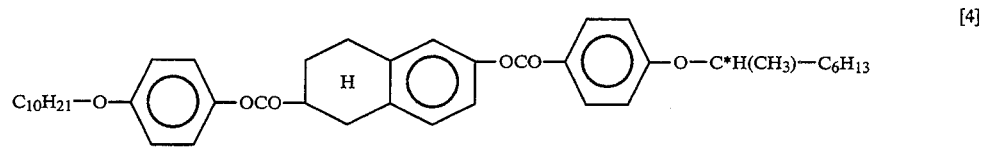

[4]

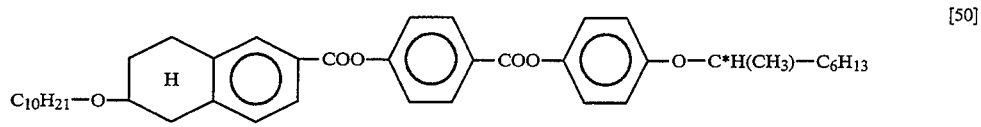

[50]

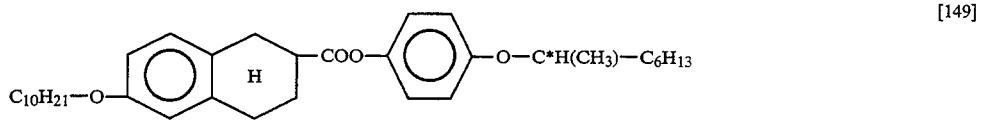

[149]

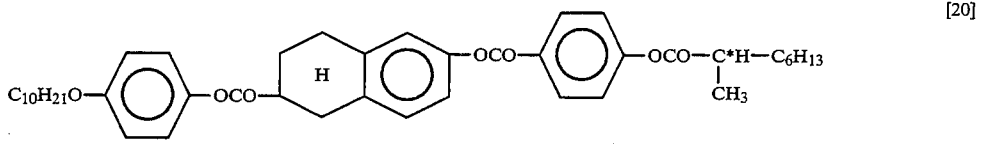

Figure 3:
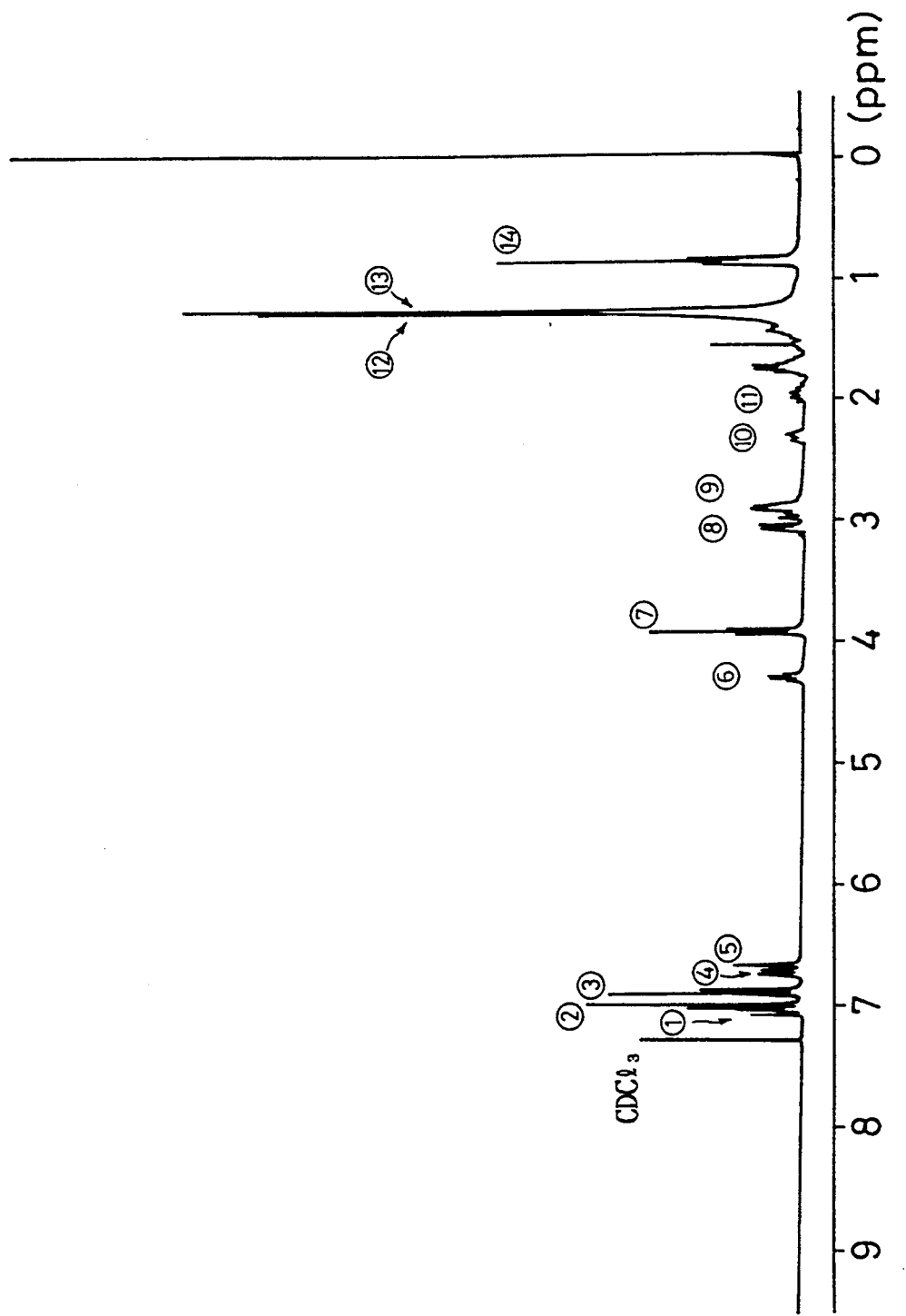
FIG. 3 shows a 1H-NMR spectrum of 6-decyloxy-1,2,3,4-tetrahydronaphthalene-2-carboxylic acid-4'-(R-2''-octyloxy)phenyl ester [Exemplified Compound (149).

[20]

phenyl ester [Exemplified Compound (149)] represented by the following formula, which is also one example of the tetralin compound of the invention, is shown in FIG. 3.

Phase transition temperatures of the compounds represented by the formulas [4], [50]and [149] which are particularly excellent as liquid crystal compounds are shown in Table 3, wherein Cry, SmC$_A$* SmC* SmA, Ch

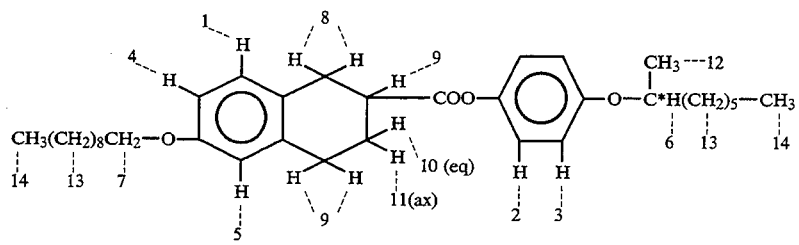

In the above formula, each of numbers 1 to 14 indicates hydrogen atom, and each of the numbers corresponds to the same number attached to either one of peaks shown in FIG. 3.

and Iso denote a crystal phase, an antiferroelectric phase, a ferroelectric phase, a smectic A phase, a cholesteric phase and an isotropic liquid, respectively.

TABLE 3

| | Cry—SmC$_A$* or SmC*—CmA | SmC$_A$*—SmA or Ch | SmA—Iso or Ch |
|---|---|---|---|
| [4] | 40° C. SmC$_A$* | 82° C. Ch | 103° C. |
| [50] | 40° C. SmC* | 59° C. SmA | 108° C. |
| [149] | 21° C. SmA | — | 34° C. |

In the liquid crystal compounds of the invention, there are many compounds exhibiting a smectic phase over a broad temperature range, as shown in Table 3.

There have been known few liquid crystal compounds which, if used alone as a liquid crystal material, exhibit a smectic phase over such a broad temperature range as in the above-mentioned compounds. In addition to the fact that the liquid crystal material of the invention exhibits a smectic phase in a broad temperature range, a liquid crystal element filled with such liquid crystal material, for example, an optical switching element, is excellent in high response speed.

The liquid crystal material of the invention may be used either singly or in a mixture with other liquid crystal material in the form of a liquid crystal composition. For example, the liquid crystal material of the invention may be used as a major component of a ferroelectric or antiferroelectric liquid crystal composition or as a minor component of a liquid crystal composition which exhibits a smectic phase. That is, of the tetralin compounds of the invention, a tetratin compound exhibiting a smectic phase can be used as a major component of a liquid crystal composition or a minor component of a liquid crystal composition which contains other liquid crystal material as a major component, while a tetralin compound which does not exhibit a smectic phase can be used as an assistant of a liquid crystal composition which contains other liquid crystal material as a major component.

The liquid crystal composition of the present invention comprises the tetralin compound of the formula [I] and a liquid crystal compound other than the tetralin compound.

Examples of liquid crystal compounds which may be used in the invention in combination with the compound represented by the formula [I] include those listed below.

(+)-4'-(2''-methylbutyloxy)phenyl-6-octyloxynaphthalene-2-carboxylate,

4'-decyloxyphenyl-6-((+)-2''-methylbutyloxy)naphthalene-2-carboxylate,

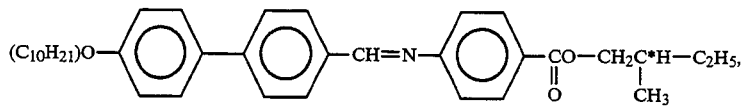

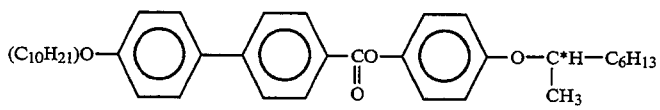

and

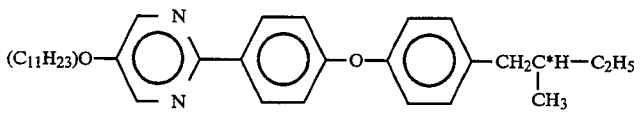

In addition to the above, there may be mentioned the following compounds having a cyclic structure and an optical activity.

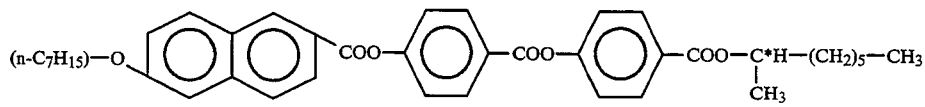

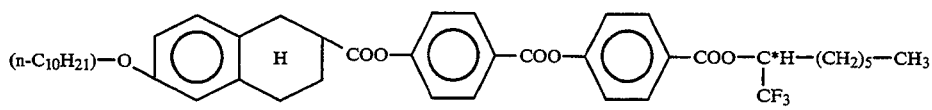

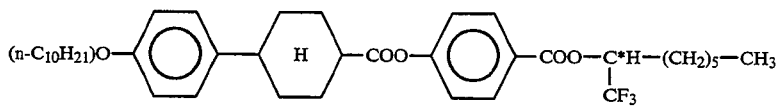

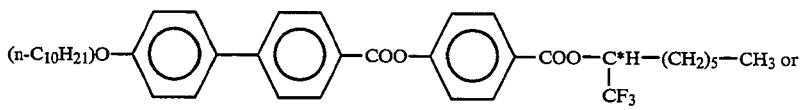

-continued

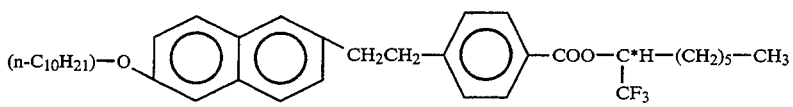

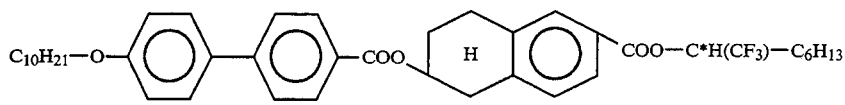

Further, there also may be mentioned Schiff base type liquid crystal compounds such as

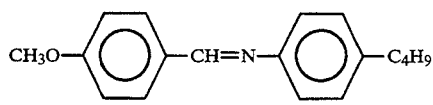

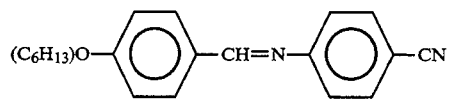

azoxy type liquid crystal compounds such as

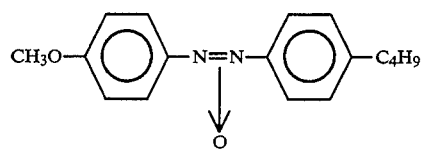

benzoate type liquid crytal compounds such as

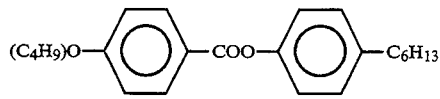

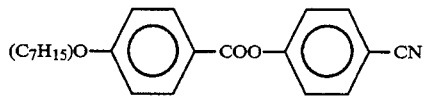

cyclohexylcarboxylate type liquid crystal compounds such as

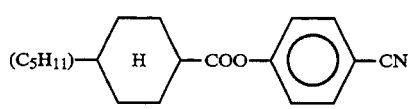

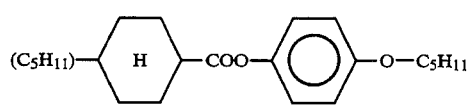

phenyl type liquid crystal compounds such as

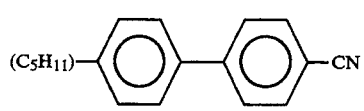

terphenol type liquid crystal compounds such as

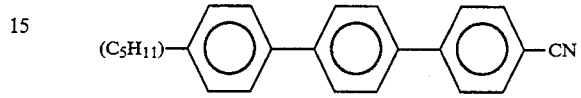

cyclohexyl type liquid crystal compounds such as

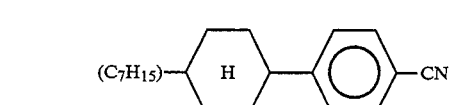

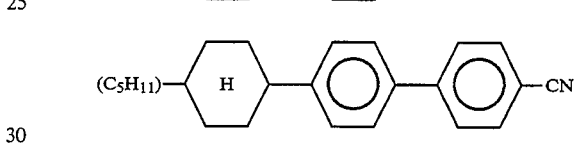

and pyrimidine type liquid crystal compounds such as

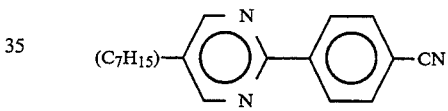

An amount of the tetralin compound of the formula [I] contained in the liquid crystal composition can be optionally determined in consideration of characteristics of the resulting composition. The composition of the invention contains the tetralin compound of the formula [I] in an amount of usually 1–99 parts by weight, preferably 5–75 parts by weight, based on 100 parts by weight of the total amount of liquid crystal materials contained in the composition.

In addition to the liquid crystal materials mentioned as above, the liquid crystal composition may further contain additives which are conventionally used in liquid crystal compositions, for example, conductivity-imparting agents and life-improving agents.

The liquid crystal composition of the invention can be prepared by mixing the above-mentioned tetralin compound with other liquid crystal material, and if desired, additives.

When a voltage is applied to the liquid crystal composition comprising the above-mentioned liquid crystal material, an optical switching phenomenon takes place. Utilizing this phenomenon, a display device exhibiting a good response can be produced. In the invention, with regard to elements utilizing such phenomenon or methods of driving the elements, reference to for example Japanese Patent L-O-P Publns. Nos. 107216/1981 and 118744/1984 may be made.

The liquid crystal material that may be used in the display device referred to above may include such compounds as exhibiting any of smectic C phase, smectic F phase, smectic G phase, smectic H phase, smectic I phase, smectic J phase and smectic K phase. Display devices using liquid crystal materials exhibiting other phases than the smectic C phase generally have a low response speed, and hence it has heretofore been considered that it is effective to drive a display device by means of a liquid crystal material exhibiting the smectic C phase having a high response speed.

However, it has been found that it is possible in the invention to advantageously use the liquid crystal material even when it exhibits a smectic A phase other than the smectic C phase by utilizing a method in which the display device is driven by means of a liquid crystal material exhibiting a smectic A phase as proposed by the present inventors in Japanese Patent L-O-P Publn. No. 3632/1989. That is, by virtue of utilization of this driving method, the liquid crystal element of the invention can be driven in a wide phase range, and at the same time, it is possible to speed up an electro-optical response.

Figure 6:
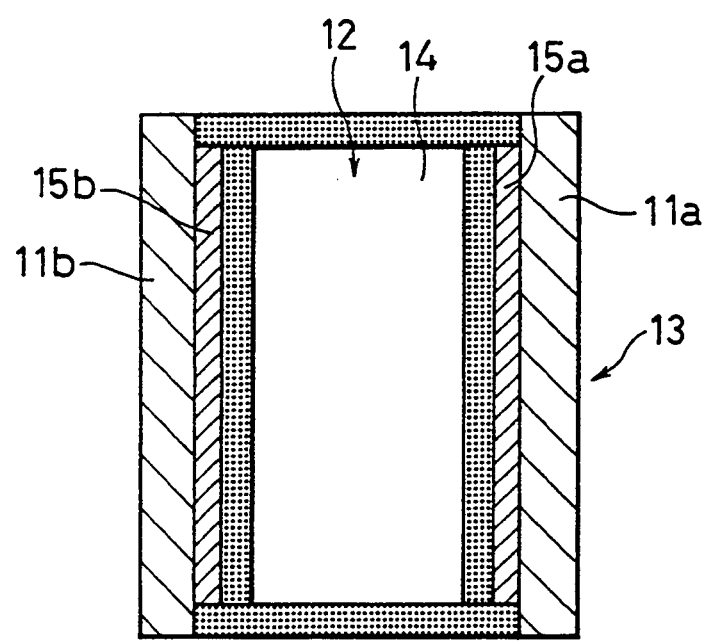
FIG. 6 is a schematic sectional view of a liquid crystal element of the present invention.

The liquid crystal element of the invention comprises a cell filled with a liquid crystal material or composition, and polarizing plates. In detail, the liquid crystal element of the invention, for example, as shown in FIG. 6, is formed from a cell 13 comprising two transparent substrates 11a and 11b arranged so as to form a gap 14 to be filled with a liquid crystal material 12, and transparent electrodes 15a and 15b formed on the surfaces of the transparent substrates 11a and 11b, said surfaces individually facing the liquid crystal material 12, the liquid crystal material 12 charged in the gap 14 of the cell 13, and two polarizing plates (not shown in FIG. 6) each arranged on an outer side of the cell 13.

In the invention, employable as the transparent substrate are, for example, glass and transparent polymer plates. When glass substrates are used, the substrate surfaces may be provided with an undercoat layer (i.e., a layer for inhibiting permeation of unnecessary component) comprising silicon oxide as a major component to prevent deterioration of the liquid crystal material caused by elution of alkali component of the glass. The transparent substrate, for example, glass substrate, usually has a thickness of 0.01-1.0 mm.

In the invention, flexible transparent substrates may be used as the transparent substrates. In this case, one of the substrates may be a flexible transparent substrate, or both substrates may be flexible transparent substrates. Useful as such flexible transparent substrates are polymer films. When the flexible transparent substrates are used as the transparent substrates of the invention, it is preferred that a thickness t (mm) of each flexible transparent substrate, a modulus of elasticity E (kgf/m²) and a width a (mm) of the gap formed in the cell have the following relationship.

$$\frac{a^4}{Et^3} < 0.32$$

On the surface of each transparent substrates, a transparent electrode is provided. The transparent electrode is formed, for example, by coating the transparent substrate surface with iridium oxide, tin oxide, etc. The transparent electrode can be formed by a known method. The thickness of the transparent electrode is usually in the range of 100 to 2,000 Å.

The transparent substrate having the transparent electrode may be further provided with an orientation layer or a ferroelectric material layer on the surface of the transparent electrode. The orientation layer includes, for example, an organic thin film formed by chemical adsorption thereon of an organic silane coupling agent or a carboxylic acid polynuclear complex, and an inorganic thin film. Examples of the organic thin film include thin films of polymers such as polyethylene, polypropylene, polyester, polyamide, polyvinyl alcohol and polyimide. The organic thin film may be formed by such techniques as coating, adhesion, deposition or polymerization (e.g., plasma polymerization) on the substrate.

Examples of the inorganic thin film include thin films of oxides such as silicon oxide, germanium oxide and alumina, thin films of nitrides such as silicon nitride, and thin films of other semi-conductors. The inorganic thin film may be formed by such techniques as deposition (e.g. rhombic deposition) and sputtering.

The thin film as mentioned above is imparted with orientation by imparting anisotropy or stereospecificity to the thin film itself in the film forming procedure, or externally imparting orientation to the thin film after the film forming procedure. In concrete, there may be mentioned a method in which the thin film is formed by coating a polymer material such as polyimide resin on the transparent electrode, followed by rubbing the film in a definite direction; a method in which a polymer film is subjected to stretching to impart orientation to the stretched film; and a method in which an oxide is subjected to rhombic deposition to form the oriented oxide film.

Such thin film (e.g, orientation layer) may be so formed that it also serves as a spacer described later.

Two of the transparent substrates as mentioned above are arranged in such a manner that the transparent electrodes formed on the substrates face each other and a gap to be filled with a liquid crystal material (or composition) is formed by these two transparent substrates. The gap thus formed has a width of usually 1-10 μm, preferably 1-5 μn. The gap may be formed, for example, by arranging the two substrates so as to hold a spacer therebetween. Usable as the spacer is a polyimide type polymer material which is obtained, for example, by patterning a photosensitive polyimide precursor. By the use of the spacer, a monodomain is formed by the interfacial effect between the spacer and the liquid crystal material.

Figure 7A:
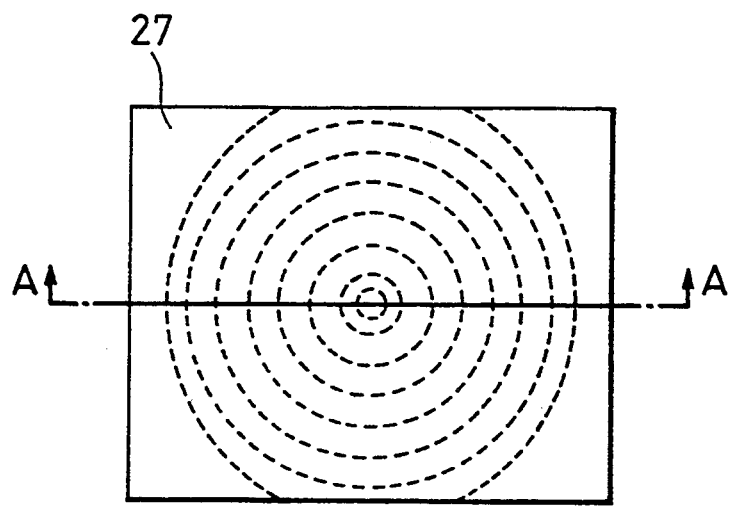
FIG. 7 (a) shows a liquid crystal element having a concentric spacer, and FIG. 7 (b) is a sectional view taken on line A—A of FIG. 7 (a).
Figure 7B:
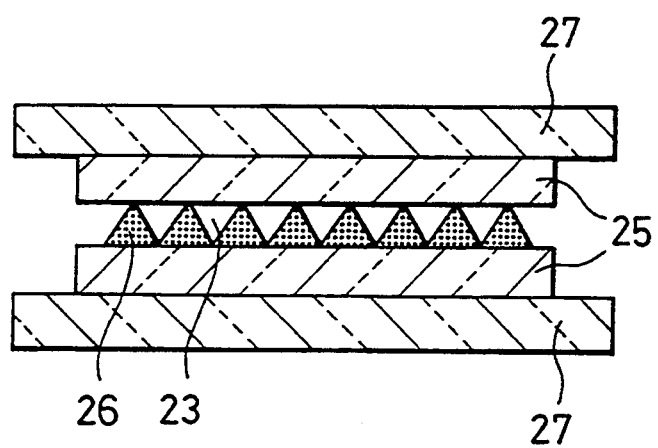

As shown in FIG. 7 (a) and FIG. 7 (b) that is a sectional view taken on line A—A of FIG. 7 (a), integration of the orientation film with the spacer may be made, for example, by using a concentric spacer 26 which acts as an orientation film. In FIG. 7 (a) and FIG. 7 (b), the transparent substrates are indicated by numeral 27, the transparent electrodes are indicated by numeral 25, and the liquid crystal material is indicated by numeral 23.

Figure 8A:
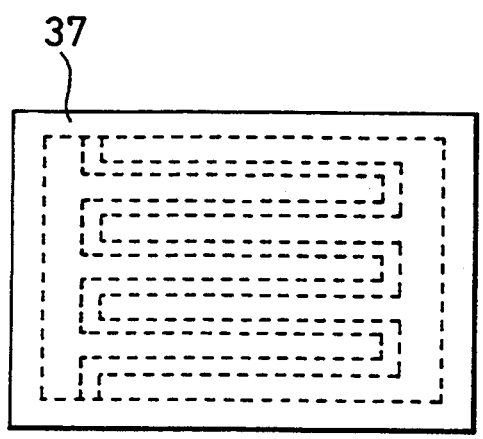
FIG. 8 (a) shows a liquid crystal element having a comb-like spacer, and FIG. 8 (b) is a sectional view taken on line A—A of FIG. 8 (a).
Figure 8B:
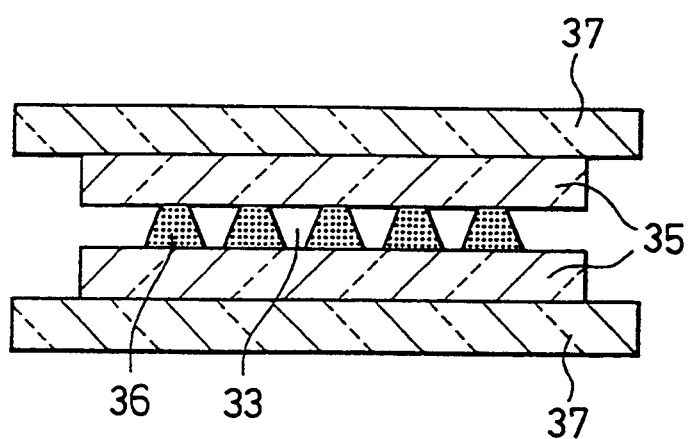

As shown in FIG. 8 (a) and FIG. 8 (b) that is a sectional view taken on line A—A of FIG. 8 (a), integration of the orientation film with the spacer may be made, for example, by using a comb-like spacer 36 which acts as an orientation film. In FIG. 8 (a) and FIG. 8 (b), the transparent substrates are indicated by numeral 37, the transparent electrodes are indicated by numeral 35, and the liquid crystal material is indicated by numeral 33.

Figure 9:
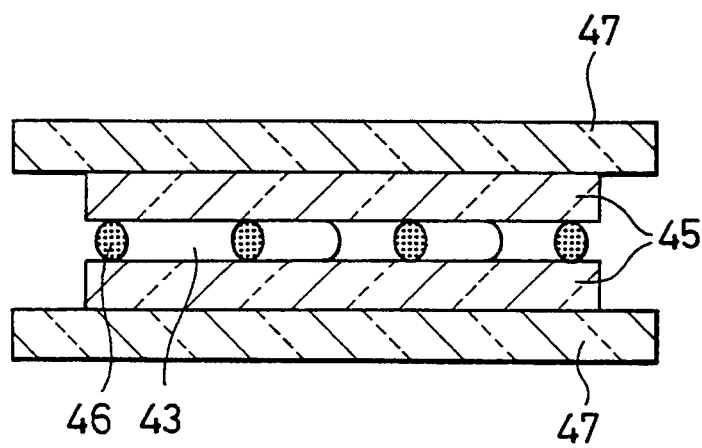
FIG. 9 is a sectional view showing a structure of a liquid crystal element of the present invention in which a fiber is used as a spacer.

As shown in FIG. 9, fibers 46 may be incorporated into a liquid crystal material 43 instead of using the above-mentioned spacer. In this case, a definite gap is held between transparent substrates 47 each provided with a transparent electrode 45 owing to the fibers.

The fibers used herein preferably have the following relationship between an average diameter and an average length of the fibers.

$$3 \leq \frac{q}{d} \leq 100$$

wherein d is an average diameter of the fibers, and q is an average length of the fibers.

Various kinds of fibers are employable as the fibers, but preferred are those obtained by spinning alkali glass.

It is also possible to incorporate particulate materials into the liquid crystal material in place of or in combination with the above-mentioned fibers.

The particulate materials include those of melamine resin, urea resin or benzoguanamine resin having a particle diameter of 1–10 μm.

The two transparent substrates arranged so as to form the gap in the manner described above are combined together by sealing their peripheries with a sealer. Useful as the sealer are, for example, epoxy resin and silicone resin. The epoxy resin or the like used as the sealer may be modified with acrylic materials or silicone rubbers.

The gap of the liquid crystal cell having such a structure as mentioned above is filled with a liquid crystal material (or composition) comprising the tetralin compound represented by the formula [I].

The liquid crystal material filled in the gap of the liquid crystal cell can be oriented, for example, by utilizing a monoaxial orientation control method such as a temperature gradient method using a spacer edge or a surface treatment method using an orientation film. In the invention, it is also possible to carry out initial orientation of the liquid crystal material, for example, by applying a direct bias voltage to the liquid crystal material while heating the material.

Figure 10:
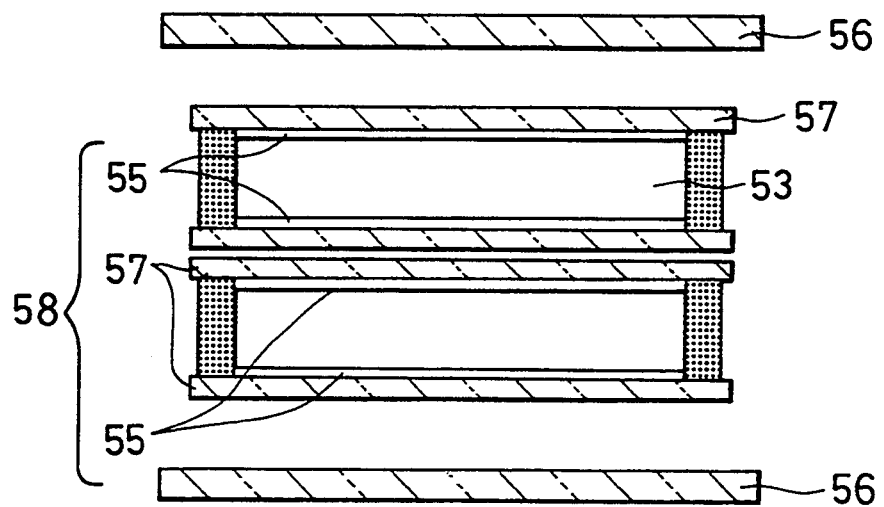
FIG. 10 is a sectional view showing a structure of a liquid crystal element of the invention in which a cell is disposed between two polarizing plates.

The liquid crystal cell filled with the liquid crystal material and subjected to initial orientation as described above is disposed between two polarizing plates. As shown in FIG. 10, two or more of cells 58 each of which comprises two transparent substrates 57 and two transparent electrodes 55 and is filled with a liquid crystal material 53 may also be disposed between two polarizing plates 56.

In the liquid crystal element of the invention, two polarizing plates can be disposed so that planes of polarization of the polarizing plates meet at an angle of 70°–110°. Preferably, the polarizing plates are disposed so that the directions of polarized lights of the two polarizing plates meet at right angles, namely, at an angle of 90°.

Usable as the polarizing plates are polarizing films which are imparted with polarizing properties by stretching a resin film such as a polyvinyl alcohol resin film or a polyvinyl butyral resin film in the presence of iodine or the like so as to allow the film to absorb the iodine. The polarizing film may have a multi-layer construction by coating its surface with other resin.

In the present invention, the above-mentioned liquid crystal cell may be disposed between two polarizing plates having been arranged as described above so that a rotation angle of the cell is within the range of ±10° based on the state wherein an amount of the transmitted light is the least (i.e., the darkest state), preferably the darkest state is attained. The liquid crystal cell may also be disposed between the polarizing plates having been arranged as described above so that a rotation angle of the cell is within the range of ±10° from the state wherein an amount of the transmitted light is the most (i.e., the brightest state), preferably the brightest state is attained.

The liquid crystal element of the invention can be prepared, as shown in FIG. 6, by filling the gap 14 of the cell 13 with the liquid crystal material 15 mentioned as above and subjecting the crystal material 15 to initial orientation.

The liquid crystal material 15 is usually heated until it reaches a molten state, and the molten material is injected into the vacuumized gap 14 of the cell 13 through an inlet provided in the cell. After the injection operation, the inlet is sealed.

After sealing the inlet, the cell 13 is heated to a temperature higher than the temperature at which the liquid crystal material 15 filled in the cell 13 exhibits an isotropic phase, and then the cell is cooled to a temperature at which the liquid crystal material 15 exhibits a liquid crystal phase.

The cooling is carried out at a rate of, preferably not more than 2° C./min, more preferably 0.1°–2.0° C./min, particularly preferably 0.1°–0.5° C./min. By cooling the cell 13 at such a cooling rate as mentioned above, the state of initial orientation of the liquid crystal material 15 is improved, and thereby a liquid crystal element having a liquid crystal phase consisting of a monodomain of less orientation defect can be easily prepared. The initial orientation referred to herein implies the state of arrangement of the liquid crystal material prior to changing orientation vector of the liquid crystal material by applying a voltage to the material.

The liquid crystal element of the invention prepared as above is markedly excellent in characteristics such as contrast as compared with conventional liquid crystal elements, and hence the element of the invention can be favorably used as, for example, a surface stabilized ferroelectric liquid crystal element, a helical modulation element, an excess scattering element, a guest-host type element and a vertical orientation liquid crystal element.

In the case where the liquid crystal element of the invention is driven by applying thereto an electric field, the electric field is controlled to have a frequency of usually 1 Hz to 100 KHz, preferably 10 Hz to 10 KHz, and to have a voltage of usually 0.01 to 60 Vp-p/μm$^t$ (voltage per thickness of 1 μm), preferably 0.05 to 30 Vp-p/μm$^t$.

When the liquid crystal element of the invention using an optically active liquid crystal material which comprises the tetralin compound represented by the aforementioned formula [I] is driven by application of an electric field, two kinds of hysteresis curves of the transmitted light through the liquid crystal element are drawn, by changing a width of the wave (driving wave) of the electric field to be applied. One of the hysteresis curves is drawn by a driving method in which a so-called bi-stability of the liquid crystal material is utilized, and the other is a curve drawn by a driving method in which a so-called tri-stability of the liquid crystal material is utilized.

The liquid crystal element of the invention in which a liquid crystal cell filled with the optically active liquid crystal material is disposed between two polarizing plates which are arranged so that the polarizing planes meet at right angles and the darkest state is attained when no electric field is applied, may be driven, for example, by application of an electric field of any wave form having a frequency of 50 Hz to 100 KHz, preferably 70 Hz to 10 KHz, such as rectangular wave (or pulse wave), triangular wave, sine wave and a combination thereof. For example, when an electric field of rectangular wave or pulse wave or combination thereof is applied, the driving speed of the liquid crystal element can be increased by setting a width of the electric field to not more than 10 millisec., preferably within a range of 0.01 to 10 millisec. In this range, the liquid crystal element of the invention can be used as a liquid crystal element having a bi-stability. On the other hand, by setting the width of the electric field to more than 10 millisec., preferably within a range of 33 to 1,000 millisec., the liquid crystal element of the invention can be used as a liquid crystal element having a tri-stability in the region where not so high driving speed is required. The term "width of the electric field" used herein means that, in the electric field of rectangular wave, for example, the time span for which a designated voltage is maintained.

By using the liquid crystal element of the invention, various liquid crystal display devices and electro-optical display devices can be manufactured. The liquid crystal element of the invention which is filled with a liquid crystal material exhibiting a smectic phase may be used for manufacturing a memory-type liquid crystal display device or an electro-optical display device incorporated with, for example, a thermal-write or laser-write type liquid crystal display element. Further, in addition to the above-mentioned uses, by the use of a liquid crystal material comprising the tetralin compound having ferroelectricity, there can be manufactured a liquid crystal display device or an electro-optical display device incorporated with, for example, an optical switching element for an optical shutter or a liquid crystal printer, a piezoelectric element and a pyroelectric element.

That is, the liquid crystal material of the invention exhibits the tri-stability or bi-stability, and hence the liquid crystal element of the invention can be allowed to have optical switching function or display function by inverting the electric field so as to attain the tri-stable state and bi-stable state.

The liquid crystal material exhibiting the bi-stability has a spontaneous polarization, and hence when a voltage is applied once to the liquid crystal element comprising this liquid crystal material, the liquid crystal element keeps a memory effect even after elimination of the electric field. That is, it is not necessary to apply continuously the electric field to the liquid crystal element in order to keep this memory effect. Accordingly, in the display device using the liquid crystal element of the invention, the consumption of electric power can be reduced. Also in the case of the liquid crystal element comprising the liquid crystal material exhibiting the tristability, the memory effect can be maintained. Moreover, a display device using such liquid crystal element is very clear because of stable contrast.

Further, in the switching element of the invention comprising the liquid crystal material represented by the aforementioned formula [I], it is possible to perform switching operation only by changing the direction of orientation of the molecule. In this case, the first order of the electric field strength acts on the driving of the switching element, and hence the switching element of the invention can be driven at a low voltage.

By using this switching element, a high speed response of not longer than several 10 $\mu$ seconds can be attained, and hence the operating time of the element can be shortened sharply. Accordingly, a display (liquid crystal display device) having large numbers of scanning lines and a large screen can be easily manufactured by using the liquid crystal element of the invention. Moreover, this display can be driven without using an auxiliary means for controlling a driving temperature, because it can be driven at room temperature or lower.

Further, when an electric field is applied to the liquid crystal material of the invention, inclination of the molecule of the material is induced even in a smectic A phase which has been generally considered not to exhibit a bi-stability, and hence optical switching can be performed in this phase by utilizing such properties of the liquid crystal material. That is, it has been considered that when ferroelectric liquid crystal compounds are used, a practical response speed cannot be attained, and the smectic A phase thereof is not used generally. However, it is possible to drive a display device using the liquid crystal element of the invention by utilizing a driving method and an apparatus proposed by the present inventors in Japanese Patent L-O-P Publn. Nos. 3632/1989 and 918/1990. Further, the liquid crystal material used in the invention exhibits two or more stable states even in the smectic F phase which is in better order than the smectic C phase, and hence optical switching can be performed in the same manner as described above by utilizing plural stable states in this phase.

The display device using the liquid crystal element of the invention may be driven by various methods, and concrete examples of those methods are described below.

The first method comprises interposing the liquid crystal element of the invention between two polarizing plates, applying an external voltage to the liquid crystal element to change an orientation vector of the liquid crystal material filled in the element, and thereby performing display utilizing birefringence caused by the two polarizing plates and the liquid crystal material.

The second method is to utilize dichroism of a dichromic dye incorporated in a liquid crystal material. This method is to perform display by changing the orientation direction of the liquid crystal compound to cause a change of wavelength of light absorbed by the dye. The dye which may be used in this case generally is a dichromic dye, and examples thereof include azo dyes, naphthoquinone dyes, cyanine dyes and anthraquinone dyes.

The display device prepared by using the liquid crystal element of the invention may be driven by an electric address display system, an optical address display system, a heat address display system and a light beam display system, wherein any of driving means such as static drive, simple matrix drive and composite matrix drive may be employed.

Figure 11A:
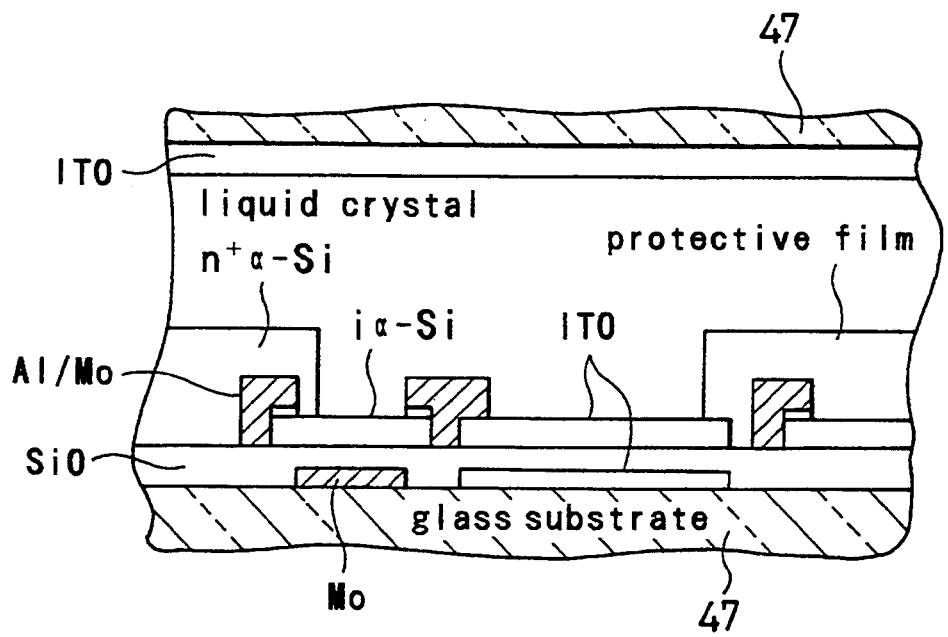
FIG. 11 (a) shows an example of a nonlinear element, and FIG. 11 (b) shows an example of a three-terminal element.
Figure 11B:
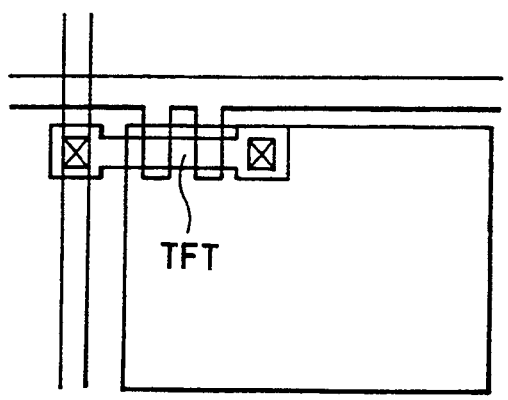

Further, when the display device in the invention is driven by application of an electric field, a nonlinear element or an active element can be used as an element for driving each picture element. More particularly, as a nonlinear element of two-terminal element, there may be mentioned, for example, an element utilizing nonlinearities of a varistor, MIM (Metal Insulator Metal) and diode arranged on one transparent substrate, as shown in FIG. 11 (a). Further, as an active element of three-terminal element, there may be mentioned, for example, an element in which TFT (thin film transistor), Si-MOS (Si-metal oxide semiconductor field-effect transistor) or SOS (Silicon on Sapphire) is arranged on a picture element, as shown in FIG. 11 (b).

EFFECT OF THE INVENTION

As described above, a novel tetralin compound is provided by the present invention.

The novel tetralin compound is optically active. Further, in the compound, 1,2,3,4-tetrahydronaphthalene ring and benzene ring are linked by means of an ester linkage, and when two benzene rings exist, these benzene rings are also linked by means of an ester linkage. For these reasons, the tetralin compound exhibits a smectic phase over a wide temperature range including room temperature, and can be used as a ferroelectric liquid crystal material or an antiferroelectric liquid crystal material.

By combining the liquid crystal material of the invention with the same or different kind of liquid crystal material, the temperature range where the liquid crystal exhibits effective properties can be widened without marring ferroelectricity or antiferroelectricity of the liquid crystal material of the invention.

Accordingly, by the use of such liquid crystal material, a liquid crystal element having a high speed response in a wide temperature range can be obtained.

Further, in a liquid crystal display prepared by using such element, the operating time can be shortened sharply. In addition, the consumption of electric power can be reduced, and a high contrast and a stable contrast can be obtained. Moreover, the liquid crystal display can be driven at a low voltage.

When the tetralin compound of the invention is used as an antiferroelectric liquid crystal compound, the memory characteristics may be obtained without difficulty, and the orientation characteristics may also be improved.

By the use of the liquid crystal material of the invention, there can be obtained various devices having excellent characteristics such as wide operating temperature range, high switching speed, very small consumption of electric power and stable contrast.

The present invention is further described below with reference to examples, but it should be construed that the invention is in no way limited to those examples. In the examples, R and S mean R body and S body of an optically active compound, respectively.

EXAMPLE 1

Synthesis of
6-[4'-(R-2''-Octyloxy)Benzoyloxy]-1,2,3,4-Tetrahydronaphthalene-2-Carboxylic
Acid-4'''-Decyloxyphenyl Ester [Exemplified Compound (4)]

First Stage

To a mixture of 3.86 g (11.8 mmol) of 6-decyloxynaphthalene-2-carboxylic acid and 130 ml of 1,2-diethoxyethane was added 3.0 g (130 mg atom) of metallic sodium with stirring at 120° C. in a nitrogen atmosphere, and the resulting mixture was heated to a reflux temperature.

To the mixture was dropwise added 10 g (114 mmol) of isoamyl alcohol over 1 hour, and they were reacted with each other for 11 hours under reflux. After cooling of the reaction system to room temperature, to the reaction mixture was added ethanol to change the remaining metallic sodium to sodium alcoholate. Then, the reaction mixture was made acidic using 20% hydrochloric acid.

To the reaction mixture was added 100 ml of water, then the resulting organic phase was separated from the mixture, and the organic phase was washed with water.

The organic phase was concentrated under a reduced pressure to obtain 4.25 g of a solid. This solid was recrystallized with toluene to obtain 2.95 g (8.89 mmol) of 1,2,3,4-tetrahydro-6-decyloxynaphthalene-2-carboxylic acid.

Second Stage

A mixture of 16.6 g (50 mmol) of the 1,2,3,4-tetrahydro-6-decyloxynaphthalene-2-carboxylic acid obtained in the first stage, 250 ml of acetic acid and 86.5 g (0.5 mol) of 47% hydrobromic acid was heated under reflux at 130° C. for 7 hours. After addition of distilled water, the mixture was concentrated under a reduced pressure to obtain 10.60 g (50 mmol) of 1,2,3,4-tetrahydro-6-hydroxynaphthalene-2-carboxylic acid.

Third Stage

A mixture of 10.60 g (50 mmol) of the 1,2,3,4-tetrahydro-6-hydroxynaphthalene-2-carboxylic acid obtained in the second stage, 12.85 g (75 mmol) of benzyl bromide, 6.6 g (100 mmol) of 85% potassium hydroxide, 0.525 g (3.5 mmol) of sodium iodide, 200 ml of ethanol and 25 ml of distilled water was heated under reflux at 100° C. for 12 hours. To the mixture was further added 50 ml of 10% potassium hydroxide, and they were heated under reflux for 2 hours. After cooling of the reaction system to room temperature, the reaction mixture was added to cold water, and the reaction mixture was made acidic using 36% hydrochloric acid.

The mixture was filtered to obtain a precipitate, and the precipitate was recrystallized with toluene to obtain 13.08 g (46.4 mmol) of 1,2,3,4-tetrahydro-6-benzyloxynaphthalene-2-carboxylic acid.

Fourth Stage

To a mixture of 0.40 g (1.4 mmol) of the 1,2,3,4-tetrahydro-6-benzyloxynaphthalene-2-carboxylic acid obtained in the third stage, 0.35 g (1.4 mmol) of hydroquinone monodecyl ether separately synthesized by a conventional process, 0.22 g (0.16 mmol) of 4-N,N-dimethylaminopyridine and 20 ml of methylene chloride was

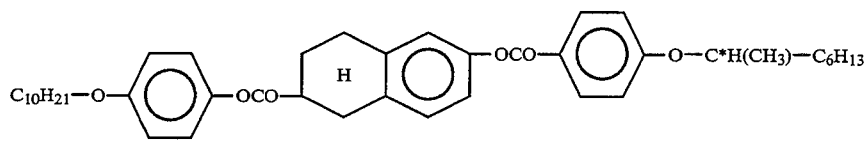

[4]

dropwise added 3 ml of a methylene chloride solution containing 0.37 g (1.8 mmol) of N,N'-dicyclohexylcarbodiimide over 1.5 hours with stirring at room temperature.

Further, the reaction was carried out at room temperature for 3.5 hours.

The reaction mixture was filtered, and the filtrate obtained was concentrated. The resulting concentrate was separated by means of column chromatography to obtain 0.61 g (1.19 mmol) of 1,2,3,4-tetrahydro-6-benzyloxynaphthalene-2-carboxylic acid-4'-decyloxyphenyl ester as a white solid.

Fifth Stage

Into a mixture of 0.61 g (1.19 mmol) of the 1,2,3,4-tetrahydro-6-benzyloxynaphthalene-2-carboxylic acid-4''-decyloxyphenyl ester obtained in the fourth stage, 0.30 g of 5% palladium/carbon and 10 ml of tetrahydrofuran was blown hydrogen gas for 16 hours with stirring at room temperature under normal pressure.

The reaction mixture was filtered using Celite as a filter aid, and the filtrate obtained was concentrated to obtain 0.44 g (1.0 mmol) of 1,2,3,4-tetrahydro-6-hydroxynaphthalene-2-carboxylic acid-4'-decyloxyphenyl ester as a white solid.

Sixth Stage

To a mixture of 0.44 g (1.0 mmol) of the 1,2,3,4-tetrahydro-6-hydroxynaphthalene-2-carboxylic acid-4'-decyloxyphenyl ester obtained in the fifth stage, 0.25 g (1.0 mmol) of 4-(R-2'-octyloxy) benzoic acid, 0.02 g (0.16 mmol) of 4-N,N-dimethylaminopyridine and 15 ml of methylene chloride was dropwise added 3 ml of a methylene chloride solution containing 0.25 g (1.2 mmol) of N,N'-dicyclohexylcarbodiimide over 1 hour with stirring at room temperature.

Further, the reaction was carried out at room temperature for 3.5 hours.

The reaction mixture was filtered, and the filtrate obtained was concentrated. The resulting concentrate was separated by means of column chromatography to obtain 0.51 g of a colorless semisolid.

This semisolid had a M/e value in FD-mass spectrum of 656.

A $^1$H-NMR spectrum of this compound is shown in FIG. 1.

From the analysis of these spectra, this compound was identified as 6-[4'-(R-2''-octyloxy)benzoyloxy]-1,2,3,4-tetrahydronaphthalene-2-carboxylic acid-4'''-decyloxyphenyl ester [Exemplified Compound (4)].

This compound had a tilt angle of 45°.

EXAMPLE 2

Synthesis of 4-(6'-Decyloxy-5',6',7',8'-Tetrahydro-2''-Naphthoyloxy)-Benzoic Acid-4''-(R-2'''-Octyloxy)Phenyl ester [Exemplified Compound (50)]

First Stage 328 mg (1.0 mmol) of 6-decyloxynaphthalene-2-carboxylic acid and 0.1 g of 5% palladium/carbon were mixed with 10 ml of tetrahydrofuran, and the resulting mixture was stirred at 120° C. and 25 atmospheric pressure in a hydrogen atmosphere.

After the temperature and the pressure of the reaction system were returned to ordinary temperature and normal pressure, the reaction mixture was filtered using Celite as a filter aid, and the filtrate obtained was concentrated. The resultant solid was recrystallized with hexane to obtain 90 mg (0.27 mmol) of 5,6,7,8-tetrahhydro-6-decyloxynaphthalene-2-carboxylic acid as a white solid.

Second Stage

To a mixture of 16.6 g (50 mmol) of the 5,6,7,8-tetrahydro-6-decyloxynaphthalene-2-carboxylic acid obtained in the first stage, 11.4 g (50 mmol) of 4-hydroxybenzoic acid benzyl ester separately synthesized by a conventional process, 0.61 g (5.0 mmol) of 4-N,N-dimethylaminopyridine and 150 ml of methylene chloride was dropwise added 50 ml of a methylene chloride solution containing 11.39 g (55 mmol) of N,N'-dicyclohexylcarbodiimide over 2 hours with stirring at room temperature.

Further, the reaction was carried out at room temperature for 3 hours.

The reaction mixture was filtered, and the filtrate obtained was concentrated. The resulting concentrate was separated by means of column chromatography to obtain 21.95 g (40.5 mmol) of 4-(5',6',7',8'-tetrahydro-6'-decyloxy-2'-naphthoyloxy)benzoic acid benzyl ester as a white solid.

Third Stage

Into a mixture of 15.37 g (28.4 mmol) of the 4-(5',6',7',8'-tetrahydro-6'-decyloxy-2'-naphthoyloxy)-benzoic acid benzyl ester obtained in the second stage, 1.54 g of 5% palladium/carbon and 100 ml of tetrahydrofuran was blown hydrogen gas for 23 hours with stirring at room temperature under normal pressure.

The reaction mixture was filtered using Celite as a filter aid, and the filtrate obtained was concentrated to obtain 12.35 g (27.3 mmol) of 4-(5',6',7',8'-tetrahydro-6'-decyloxy-2'-naphthoyloxy)benzoic acid as a white solid.

Fourth Stage

To a mixture of 0.54 g (1.0 mmol) of the 4-(5', 6',7',8'-tetrahydro-6'-decyloxy-2'-naphthoyloxy) benzoic acid obtained in the third stage, 0.22 g (1.0 mmol) of hydroquinone mono-R-2-octyloxy ether, 0.012 g (0.1 mmol) of 4-N,N-dimethylaminopyridine and 10 ml of methylene chloride was dropwise added 3 ml of a methylene chloride solution containing 0.25 g (1.2 mmol) of N,N'-dicyclohexylcarbodiimide over 1.5 hours with stirring at room temperature.

Further, the reaction was carried out at room temperature for 4 hours.

The reaction mixture was filtered, and the filtrate obtained was concentrated. The resulting concentrate was separated by means of column chromatography to obtain 0.62 g of a colorless semisolid.

This semisolid had a M/e value in FD-mass spectrum of 656.

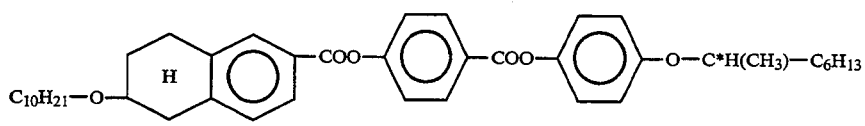

[50]

A $^1$H-NMR spectrum of this compound is shown in FIG. 2.

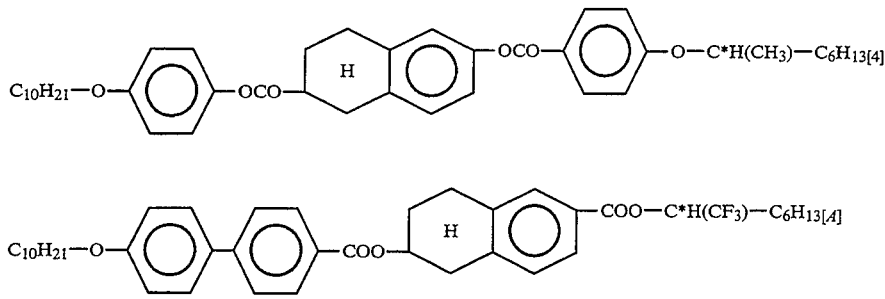

From the analysis of these spectra, this compound was identified as 4-(6'-decyloxy-5',6',7',8'-tetrahydro-2"naphthoyloxy) benzoic acid-4"- (R-2'''-octyloxy) phenyl ester [Exemplified Compound (50)].

EXAMPLE 3

Synthesis of 6-Decyloxy-1,2,3,4-Tetrahydronaphthalene-2-carboxylic acid-4'-(R-2"-Octyloxy)phenyl Ester [Exemplified Compound (149)]

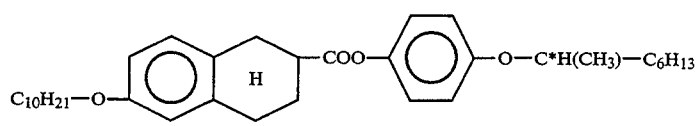

[149]

First Stage

To a mixture of 0.33 g (1.0 mmol) of 1,2,3,4-tetrahydro-6-benzyloxynaphthalene-2-carboxylic acid obtained in the same manner as described in the third stage of Example 1, 0.22 g (1.0 mmol) of hydroquinone mono-R-2-octyloxy ether, 0.02 g (0.16 mmol) of 4-N,N-dimethylaminopyridine and 15 ml of methylene chloride was dropwise added 3 ml of a methylene chloride solution containing 0.25 g (1.2 mmol) of N,N'-dicyclohexylcarbodiimide over 1 hour with stirring at room temperature.

Further, the reaction was carried out at room temperature for 5 hours.

The reaction mixture was filtered, and the filtrate obtained was concentrated. The resulting concentrate was separated by means of column chromatography to obtain 0.28 g of a colorless semisolid.

This semisolid had a M/e value in FD-mass spectrum of 536.

A $^1$H-NMR spectrum of this compound is shown in FIG. 3.

From the analysis of these spectra, this compound was identified as 6-decyloxy-1,2,3,4-tetrahydronaphthalene-2-carboxylic acid-4'-(R-2"-octyloxy)phenyl ester [Exemplified Compound (149)].

EXAMPLE 4

Preparation of Liquid Crystal Composition and Liquid Crystal Element

The compound [Exemplified Compound (4)] of the following formula which was synthesized in Example 1 and a compound [A] represented by the following formula were mixed in a mixing ratio (by weight) of 10:90, to prepare a liquid crystal composition.

A phase transition temperature of the liquid crystal composition obtained as above was measured. The result is set forth in Table 4, in which phase transition temperatures of the exemplified compound (4) and the compound [A] are also set forth.

TABLE 4

| | | | | |
|---|---|---|---|---|
| [4] | Cry 40° C. | SmC$_A$* 82° C. | Ch 103° C. | Iso |
| [A] | Cry 25° C. | SmC$_A$* 99° C. | SMa 130° C. | Iso |
| [4] (10%) + [A] (90%) | Cry 30° C. | SmC$_A$* 93° C. | SmA 129° C. | Iso |

The composition obtained as above was filled in a cell shown in FIG. 6 to prepare a liquid crystal element.

That is, the liquid crystal element was prepared in the following manner.

The above-mentioned liquid crystal composition (Exemplified Compound (4)+Compound [A]) was melted, and the molten composition was injected into the vacuumized gap of the cell wherein two orientation control films (each thickness: 150 Å) made of polyimide (Optomer AL1251 available from Japan Synthetic Rubber Co., Ltd.) and having been subjected to rubbing were formed on inner surfaces of ITO (ITO: indium tin oxide) transparent electrode substrates so that orientation control directions of the films were approximately parallel and the same directions as each other as shown in FIG. 6.

The cell filled with the liquid crystal material as described above was heated to 130° C. kept at 130° C. for 5 minutes and then cooled to 30° C. at a cooling rate of 1° C./min, to obtain a liquid crystal element.

As a result of measuring a contrast of the liquid crystal element thus obtained, the contrast was 54.

Conditions of the Cell (A) external dimension
 2.5 cm (longitudinal length)×2.2 cm (crosswise length)×1.5 mm (thickness)
(B) substrate
 thickness: 0.7 mm, material: glass
(C) distance between substrates: 2 μm
(D) side wall dimension 1.8 mm (longitudinal length)×0.1 cm (crosswise length)×2 μm (thickness)

The cell used for evaluating the liquid crystal is prepared in the following manner.

Polyimide (Optomer AL1251 available from Japan Synthetic Rubber Co., Ltd.) was subjected to spin coating at a rate of 4,000 rpm on a surface of an ITO transparent electrode which had been beforehand provided on one surface of a glass substrate. Then, the substrate was heated at 180° C. for 1 hour to harden the polyimide. The thickness of the polyimide film thus formed was in the range of 300 to 400 Å. The polyimide film was rubbed with nylon cloth in one direction to impart the polyimide film with liquid crystal orientation properties, so as to form an orientation control film.

Independently, an epoxy type adhesive (LCB-310B available from EHC Co., Ltd.), a hardening agent (LCB-310B available from EHC Co., Ltd.) and beads (GP-20 available from EHC Co., Ltd.) for ensuring a cell gap were mixed in a mixing ratio (by weight) of 130:30:3, to prepare an adhesive.

The adhesive was coated on one substrate having the orientation control film thereon by means of silk screen printing. On the substrate coated with the adhesive was placed other substrate so that the orientation control films of the two substrates faced each other, and they were heated under the following heating conditions to harden the adhesive, so as to combine the two substrates with each other.

Heating Conditions

50° C. (15 minutes)—60° C. (15 minutes)—70° C. (15 minutes)—80° C. (15 minutes)—125° C. (30 minutes)—70° C. (60 minutes)

The cell prepared as above was filled with the liquid crystal, then the cell was interposed between two polarizing plates which were arranged so that planes of polarization of the polarizing plates meet at right angles, and the cell was rotated to measure intensities of the transmitted light in the bright state and in the dark state. From the intensities of the transmitted light thus measured, a ratio of the intensity in the bright state to the intensity in the dark state (I in the bright state/I in the dark state) was calculated to determine a contrast of the element in the invention.

COMPARATIVE EXAMPLE 1

The procedure of Example 4 was repeated except for not using the exemplified compound (4) and using the compound [A] in an amount of 100% by weight, to prepare a liquid crystal element.

This liquid crystal element had a contrast of 16.

COMPARATIVE EXAMPLE 2

Synthesis of 6-[4'-R-1''-Methylheptyloxy)carbonylbenzoyloxy]-1,2,3,4-Tetrahydronaphthalene-2-Carboxylic Acid-4'''-Decyloxyphenyl Ester First Stage To a mixture of 0.28 g (1.5 mmol) of R-1-methylheptanol, 0.51 g (2 mmol) of carboxybenzoic acid benzyl ester separately synthesized by a conventional process, 0.018 g (0.15 mmol) of 4-N,N-dimethylaminopyridine and 15 ml of methylene chloride was dropwise added 7.5 ml of a methylene chloride solution containing 0.372 g (1.8 mmol) of N,N'-dicyclohexylcarbodiimide over 2 hours with stirring at room temperature.

Further, the reaction was carried out at room temperature for 48 hours.

The reaction mixture was filtered, and the filtrate obtained was concentrated. The resulting concentrate was separated by means of column chromatography to obtain 0.66 g of 4-benzyloxycarbonylbenzoic acid R-1'-methylheptyl ester.

Second Stage

Into a mixture of 0.66 g (1.5 mmol) of the 4-benzyloxycarbonylbenzoic acid R-1'-methylheptyl ester obtained in the first stage, 0.07 g of 5% palladium/carbon and 10 ml of tetrahydrofuran was blown hydrogen gas for 16 hours with stirring at room temperature under normal pressure.

The reaction mixture was filtered using Celite as a filter aid, and the filtrate obtained was concentrated to obtain 0.49 g of 4-hydroxycarbonylbenzoic acid R-1'-methylheptyl ester as a white solid.

Third Stage

To a mixture of 0.34 g (1.2 mmol) of the 1,2,3,4-tetrahydro-6-benzyloxynaphthalene-2-carboxylic acid obtained in the same manner as described in the third stage of Example 1, 0.30 g (1.2 mmol) of 4-decyloxyphenol synthesized in a conventional process, 4-N,N-dimethylaminopyridine and 12 ml of methylene chloride was dropwise added 6 ml of a methylene chloride solution containing 0.30 g (1.5 mmol) of N,N'-dicyclohexylcarbodiimide over 2 hours with stirring at room temperature.

Further, the reaction was carried out at room temperature for 48 hours.

The reaction mixture was filtered, and the filtrate obtained was concentrated. The resulting concentrate was separated by means of column chromatography to obtain 0.36 g of 1,2,3,4-tetrahydro-6-benzyloxynaphthalene-2-carboxylic acid (4'-decyloxyphenyl) ster.

Fourth Stage

Into a mixture of 0.36 g (0.07 mmol) of the 1,2,3,4-tetrahydro-6-benzyloxynaphthalene-2-carboxylic acid (4'-decyloxyphenyl)ester obtained in the third stage, 0.03 g of 5% palladium/carbon and 10 ml of tetrahydrofuran was blown hydrogen gas for 16 hours with stirring at room temperature under normal pressure.

The reaction mixture was filtered using Celite as a filter aid, and the filtrate obtained was concentrated to obtain 0.29 g (0.07 mmol) of 1,2,3,4'-tetrahydro-6-hydroxynaphthalene-2-carboxylic acid (4'-decyloxy-

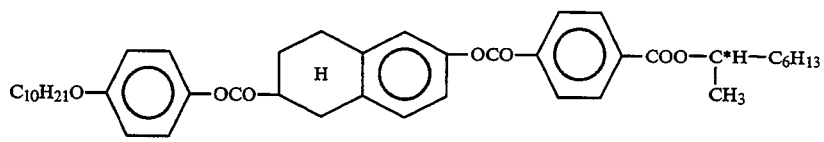

phenyl)ester as a white solid.

Fifth Stage

To a mixture of 0.13 g (0.4 mmol) of the 4-hydroxycarbonylbenzoic acid R-1'-methylheptyl ester obtained in the second stage, 0.17 g (0.4 mmol) of the 1,2,3,4-tetrahydro-6-hydroxynaphthalene-2-carboxylic acid (4'-decyloxyphenyl)ester obtained in the fourth stage, 0.005 g (0.04 mmol) of 4-N,N-dimethylaminopyridine and 10 ml of methylene chloride was dropwise added 5 ml of a methylene chloride solution containing 0.103 g (0.5 mmol) of N,N'-dicyclohexylcarbodiimide over 2 hours with stirring at room temperature.

Further, the reaction was carried out for 48 hours.

The reaction mixture was filtered, and the filtrate obtained was concentrated. The resulting concentrate was separated by means of column chromatography to obtain 0.05 g of a white solid.

This white solid had a M/e value in FD-mass spectrum of 738.

Figure 4:
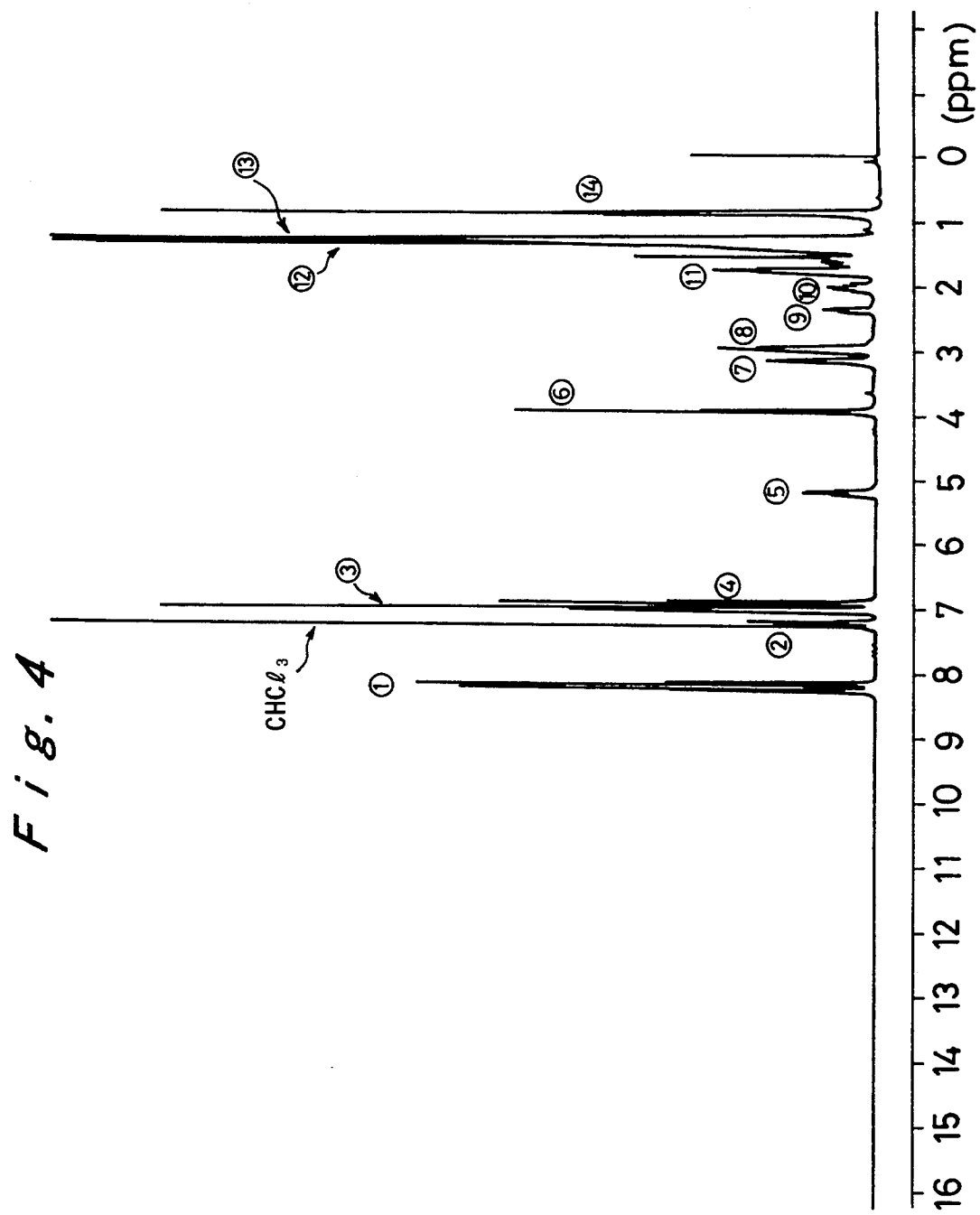
FIG. 4 shows a $^1$H-NMR spectrum of 6-[4'- (R-1'') methylheptyloxy) carbonylbenzoyloxy]-1,2,3,4-tetrahydronaphthalene-2-carboxylic acid-4'''-decyloxyphenyl ester.

A $^1$H-NMR spectrum of this compound is shown in FIG. 4.

From the analysis of these spectra, this compound was identified as 6-[4'-(R-1''-methylheptyloxy) carbonylbenzoyloxy]-1,2,3,4-tetrahydronaphthalene-2-carboxylic acid-4'''-decyloxyphenyl ester represented by the following formula.

Further, the reaction was carried out at room temperature for 48 hours.

The reaction mixture was filtered, and the filtrate obtained was concentrated. The resulting concentrate was separated by means of column chromatography to obtain 1.01 g of 4-(S-2'-methyloctanoyloxy)benzoic acid benzyl ester.

Second Stage

Into a mixture of 1.01 g (2.74 mmol) of the 4-(S-2'-methyloctanoyloxy)benzoic acid benzyl ester obtained in the first stage, 0.1 g of 5% palladium/carbon and 20 ml of tetrahydrofuran was blown hydrogen gas for 15 hours with stirring at room temperature under normal pressure.

The reaction mixture was filtered using Celite as a filter aid, and the filtrate obtained was concentrated to obtain 0.73 g of 4-(S-2'-methyloctanoyloxy)benzoic acid as a white solid.

Third Stage

A mixture of 0.28 g (1.0 mmol) of the 4-(S-2'-methyloctanoyloxy)benzoic acid obtained in the second stage, 0.13 g (1.1 mmol) of thionyl chloride, 0.2 ml of N,N-dimethylformamide and 5 ml of methylene chloride was heated with stirring under reflux for 2 hours, to obtain an yellow solution of the corresponding acid

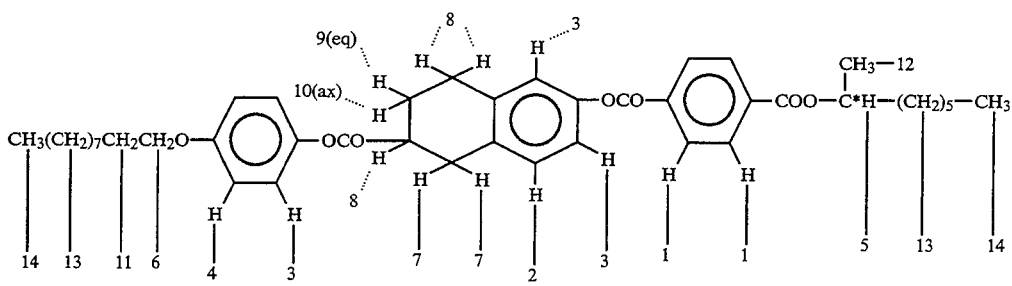

This compound had a tilt angle of 0°, and exhibited a SmA phase only.

EXAMPLE 5

Synthesis of 6-[4'-S-2''-Methyloctanoyloxy)Benzoyloxy]-1,2,3,4-Terahydronaphthalene-2-Carboxylic Acid-4'''-decyloxyphenyl ester [Exemplified Compound 20]

chloride (methylene chloride solution).

Fourth Stage

To a mixture of 0.424 g (1.0 mmol) of the 1,2,3,4-tetrahydro-6-hydroxynaphthalene-2-carboxylic acid (4'-decyloxyphenyl)ester obtained in the same manner as described in the fourth stage of Comparative Example 2, 0.40 ml of pyridine, 0.012 g (0.1 mmol) of 4-N,N-dimethylaminopyridine and 15 ml of methylene chlo-

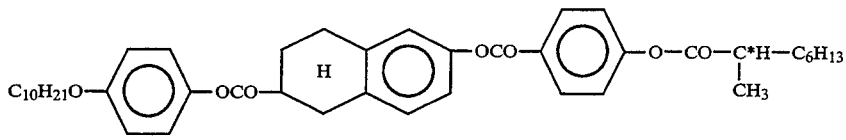

First Stage

To a mixture of 0.47 g (3 mmol) of S-2-methyloctanoic acid, 0.69 g (3 mmol) of 4-hydroxybenzoic acid benzyl ester synthesized by a conventional process, 0.037 g (0.3 mmol) of 4-N,N-dimethylaminopyridine and 30 ml of methylene chloride was dropwise added 15 ml of a methylene chloride solution containing 0.74 g (3.6 mmol) of N,N'-dicyclohexylcarbodiimide over 2 hours with stirring at room temperature.

ride was dropwise added the whole amount of the methylene chloride solution of acid chloride obtained in the third stage over 1 hour at room temperature.

Further, the reaction was carried out at room temperature for 24 hours.

The reaction mixture was introduced into water, and then extracted with ether. The ether solution obtained was concentrated. The resulting concentrate was separated by means of column chromatography to obtain 0.455 g of a white solid.

This white solid had a M/e value in FD-mass spectrum of 684.

Figure 5:
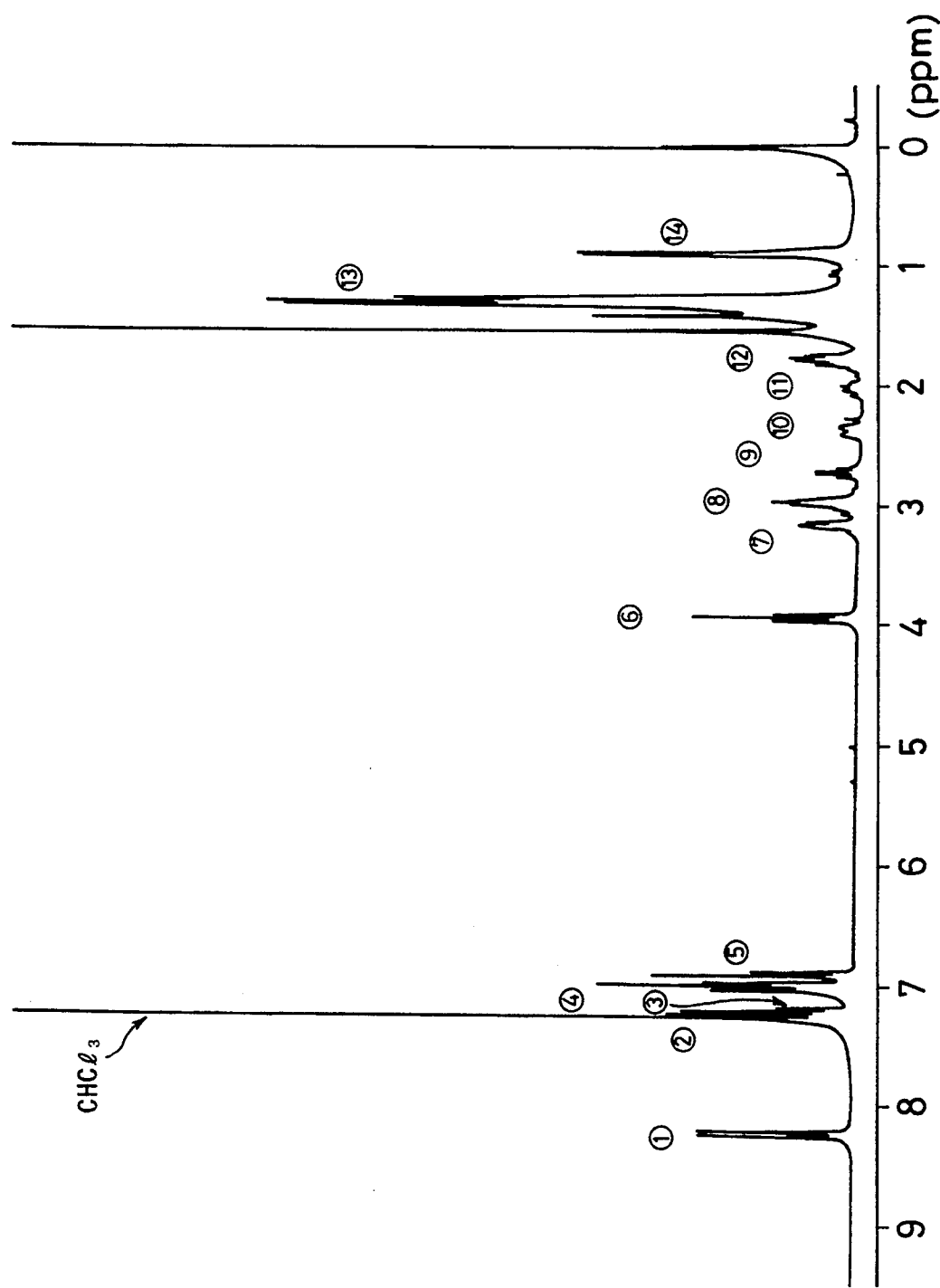
FIG. 5 shows a $^1$H-NMR spectrum of 6-[4'-(S-2''-methyloctanoyloxy) benzoyloxy]-1, 2,3,4-tetrahydronaphthalene-2-carboxylic acid-4'''-decyloxyphenyl ester [Exemplified Compound (20)].

A ¹H-NMR spectrum of this compound is shown in FIG. 5.

From the analysis Of these spectra, this compound was identified as 6-[4'-(S-2"-methyloctanoyloxy)benzoyloxy]1,2,3,4-tetrahydronaphthalene-2-carbonxylic acid-4'''-decyloxyphenyl ester (Exemplified Compound [20]) represented by the following formula.

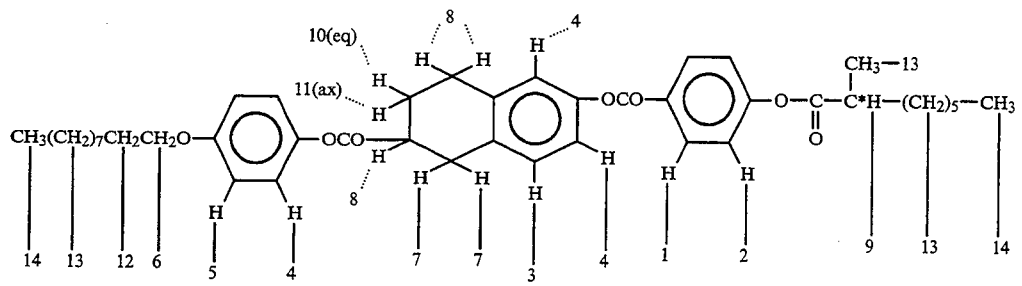

This compound had a tilt angle of 23°.

We claim:

1. A tetralin compound represented by the following formula [I]:

R—X—A¹—Y¹—A²(Y²—A³)$_n$—Z—R*  [I]

wherein
R is an alkyl group of 3–20 carbon atoms,
X is —O—CO—, —O— or a single bond,
n is 0 or 1, and
when n is 0, one of A¹ and A² is

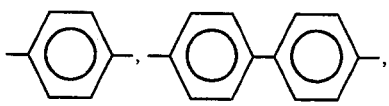

and the residual A¹ or A² is a group selected from the group consisting of

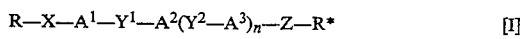

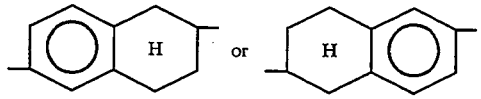

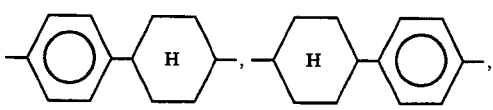

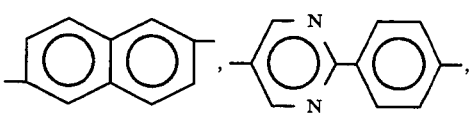

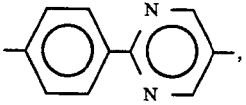

and when n is 1, one of A¹ A² and A³ is

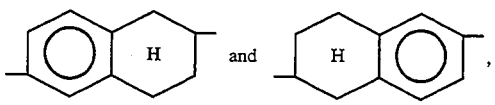

and the residual two of A¹, A² and A³ are 1,4-phenylene group,

Y¹ and Y² are each independently a group selected from the group consisting of —COO—, —O—CO—, —CH₂CH₂—, —CH₂O— and —OCH₂—, Z is —O—, —O—CO— or a single bond, and R* is a group selected from the group consisting of —C*H (CF₃) —C₆H₁₃, —C*H (CH₃) —C₅H₁₁, —C*H(CH₂H₅)—C₅H₁₁, —C*H (C₂H₅)—C₆H₁₃, —CH₂—C*H(CH₃)—C₂H₅, —(CH₂)₃—C*H(CH₃)—C₂H₅ and —C*H(CF₃)—CH₂—COO—C₂H₅.

2. The tetralin compound as claimed in claim 1, wherein Y¹ and Y² in the formula [I] are each independently —O—CO— or —COO—.

3. The tetralin compound as claimed in claim 1, wherein Z in the formula [I] is —O—.

4. A liquid crystal material comprising a tetralin compound represented by the following formula [I]:

R'X'A¹—Y¹—A²—(Y²—A³)$_n$—Z—R*  [I]

wherein
R is an alkyl group of 3–20 carbon atoms,
X is —O—CO—, —O— or a single bond,
n is 0 or 1, and
when n is 0, one of A¹ and A² is

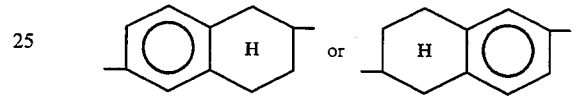

and the residual A¹ or A² is a group selected from the group consisting of

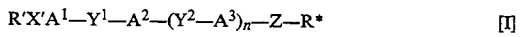

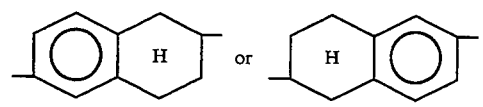

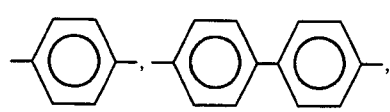

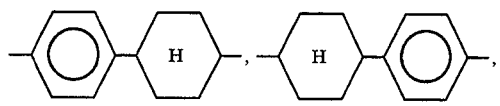

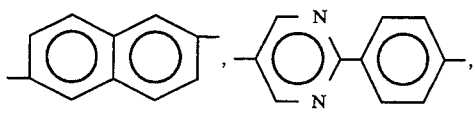

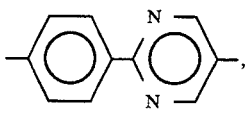

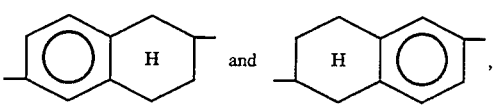

and when n is 1, one of A¹ A² and A³ is

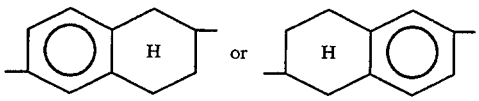

and the residual two of A¹ A² and A³ are 1,4-phenylene group,

Y¹ and Y² are each independently a group selected from the group consisting of —COO—, —O—CO—, —CH$_2$CH$_2$—, —CH$_2$O— and —OCH$_2$—, Z is —O—, —O—CO— or a single bond, and R* is a group selected from the group consisting of —C*H (CF$_3$)—C$_6$H$_{13}$, —C*H(CH$_3$)—C$_6$H$_{13}$, —C*H(CH$_3$)—C$_5$H$_{11}$, —C*H(C$_2$H$_5$)C$_5$H$_{11}$, —C*H(C$_2$H$_5$)—C$_6$H$_{13}$, —CH$_2$—C*H(CH$_3$)—C$_2$H$_5$, —(CH$_2$)$_3$—C*H(CH$_3$)—C$_2$H$_5$ and —C*H (CF$_3$) —CH$_2$—COO—C$_2$H$_5$.

5. The liquid crystal material as claimed in claim 4, wherein Y¹ and Y² in the formula [I] are each independently —O—CO— or —COO—.

6. The liquid crystal material as claimed in claim 4, wherein Z in the formula [I] is —O—.

7. A liquid crystal composition comprising a tetralin compound represented by the following formula [I]:

R—X—A¹—Y¹—A²—(Y²—A³)$_n$—Z—R*    [I]

wherein
R is an alkyl group of 3–20 carbon atoms,
X is —O—CO—, —O— or a single bond,
n is 0 or 1, and
when n is 0, one of A¹ and A² is

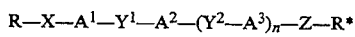

and the residual A¹ or A² is a group selected from the group consisting of

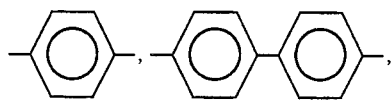

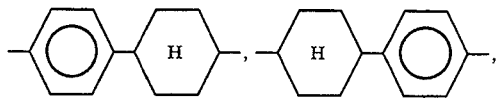

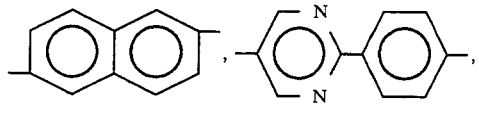

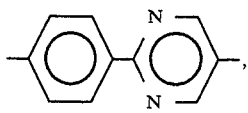

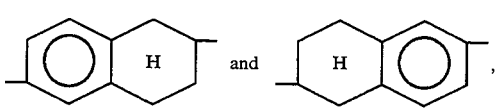

and when n is 1, one of A¹ A² and A³ is

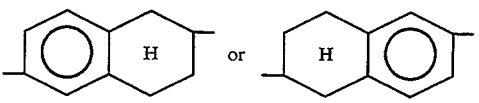

and the residual two of A¹ A² and A³ are 1,4-phenylene group,

Y¹ and Y² are each independently a group selected from the group consisting of —COO—, —O—CO—, —CH$_2$CH$_2$—, —CH$_2$O— and —OCH$_2$—, Z is —O—, —O—CO— or a single bond, and R* is a group selected from the group consisting of —C*H (CF$_3$)—C$_6$H$_{13}$, —C*H(CH$_3$)—C$_6$H$_{13}$, —C*H(CH$_3$)—C$_5$H$_{11}$, —C*H(C$_2$H$_5$)—C$_5$H$_{11}$, —C*H(C$_2$H$_5$)—C$_6$H$_{13}$, —CH$_2$—C*H(CH$_3$)—C$_2$H$_5$, —(CH$_2$)$_3$—C*H(CH$_3$)—C$_2$H$_5$ and C*H(CF$_3$) CH$_2$—COO'C$_2$H$_5$, and a liquid crystal compound other than the tetralin compound.

8. The liquid crystal composition as claimed in claim 7, wherein Y¹ and Y² in the formula [I] are each independently —O—CO— or —COO—.

9. The liquid crystal composition as claimed in claim 7, wherein Z in the formula [I] is —O—.

10. A liquid crystal element comprising a cell and a liquid crystal material, said cell comprising two substrates facing to each other and a gap formed by the substrates, said liquid crystal material being filled in the gap of the cell, in which the liquid crystal material comprises a tetralin compound represented by the following formula [I]:

R—X—A¹—Y¹—A²—(Y²—A³)$_n$—Z—R*    [I]

wherein
R is an alkyl group of 3–20 carbon atoms,
X is —O—CO—, —O— or a single bond,
n is 0 or 1, and
when n is 0, one of A¹ and A² is

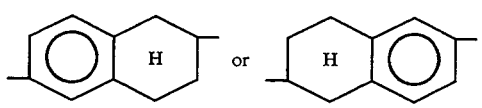

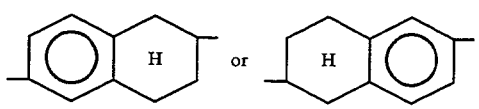

and the residual A¹ or A² is a group selected from the group consisting of

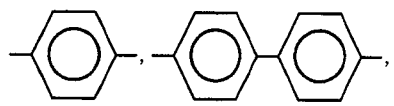

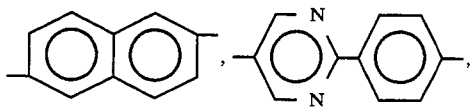

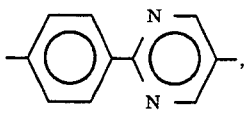

and when n is 1, one of A¹ A², and is A³ is

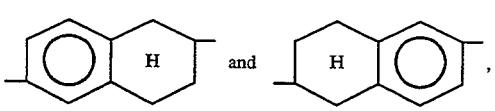

and the residual two of A¹, A² and A³ are 1,4-phenylene group,

Y¹ and Y² are each independently a group selected from the group consisting of —COO—, —O—CO—, —CH$_2$CH$_2$—, —CH$_2$O— and —OCH$_2$—, Z is —O—, —O—CO— or a single bond, and R* is a group selected from the group consisting of
—C*H(CF$_3$)—C$_6$H$_{13}$,    —C*H(CH$_3$)—C$_6$H$_{13}$,
—C*H(CH$_3$)—C$_5$H$_{11}$,    —C*H(C$_2$H$_5$)  C$_5$H$_{11}$,
—C*H (C$_2$H$_5$)—C$_6$H$_{13}$,    —CH$_2$—   C*H (CH$_3$)—C$_2$H$_5$,  —(CH$_2$)$_3$—C*H(CH$_3$)—C$_2$H$_5$ and —C*H(CF$_3$)—CH$_2$—COO—C$_2$H$_5$.

11. The liquid crystal element as claimed in claim 10, wherein Y¹ and Y² in the formula [I] are each independently —O—CO— or —COO—.

12. The liquid crystal element as claimed in claim 10, wherein Z in the formula [I] is —O—.

13. A liquid crystal element comprising a cell and a liquid crystal composition, said cell comprising two substrates facing to each other and a gap formed by the substrates, said liquid crystal material being filled in the gap of the cell, in which the liquid crystal material comprises a tetralin compound represented by the following formula [I]:

R—X—A¹—Y¹—A²—(Y²—A³)$_n$—Z—R*    [I]

wherein
R is an alkyl group of 3-20 carbon atoms,
X is —O—CO—, —O— or a single bond,
n is 0 or 1, and
when n is 0, one of A¹ and A² is

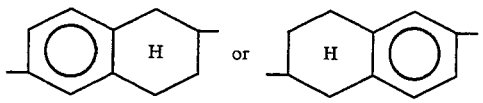

and the residual A¹ or A² is a group selected from the group consisting of

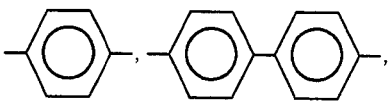

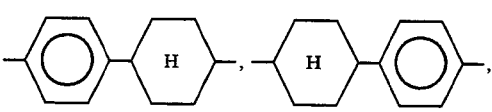

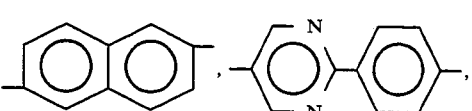

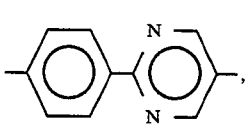

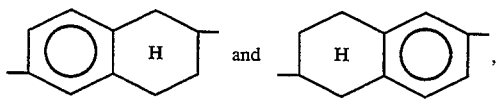

and when n is 1, one of A¹, A² and A³ is

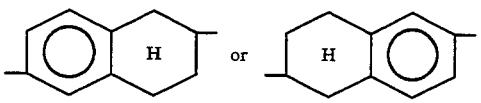

and the residual two of A¹ A² and A³ are 1,4-phenylene group,

Y¹ and Y² are each independently a group selected from the group consisting of —COO—, —O—CO—, —CH$_2$CH$_2$—, —CH$_2$O— and —OCH$_2$ —, Z is —O—, —O—CO— or a single bond, and R* is a group selected from the group consisting of
—C*H(CF$_3$)—C$_6$H$_{13}$,    —C*H(CH$_3$)—C$_6$H$_{13}$,
—C*H(CH)—C$_5$H$_{11}$,    —C*H(C$_2$H$_5$)—C$_5$H$_{11}$,
—C*H(C$_2$H$_5$)—C$_6$H$_{13}$,    —CH$_2$—C*H(CH$_3$)—C$_2$H$_5$,    —(CH$_2$)$_3$—C*H(CH$_3$)—C$_2$H$_5$ and —C*H(CF$_3$) —CH$_2$—COO—C$_2$H$_5$, and a liquid crystal compound other than the tetralin compound.

14. The liquid crystal element as claimed in claim 13, wherein Y¹ and Y² in the formula [I] are each independently —O—CO— or —COO—.

15. The liquid crystal element as claimed in claim 14, wherein Z in the formula [I] is —O—.

16. A tetralin compound represented by the following formula (I):

R—X—A¹—Y¹—A²—Z—R*   (I)

wherein
R is an alkyl group of 3–20 carbon atoms,
X is —O—CO—, —O— or a single bond,
one of A¹ and A² is

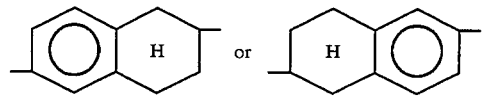

and the residual A¹ or A² is a group selected from the group consisting of

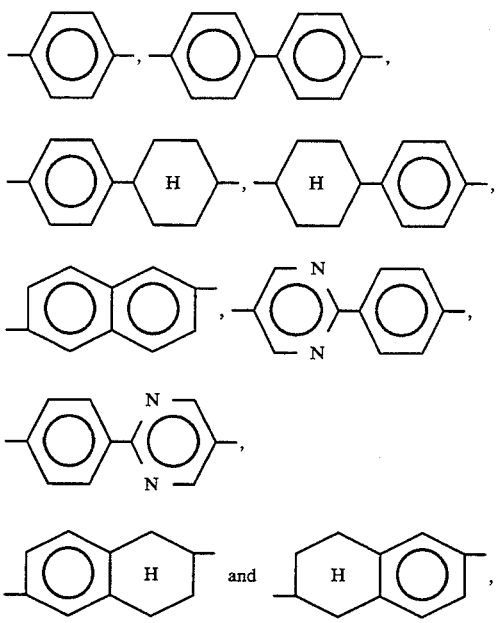

Y¹ is a group selected from the group consisting of —COO—, —O—CO—, —CH₂CH₂—, —CH₂O— and —OCH₂,
Z is —O—, —O—CO— or a single bond, and
R* is a group selected from the group consisting of
—C*H(CF₃)—C₆H₁₃,   —C*H(CH₃)—C₆H₁₃,
—C*H(CH₃)—C₅H₁₁,   —C*H(C₂H₅)—C₅H₁₁,
—C*H(C₂H₅)—C₆H₁₃,   —CH₂—C*H(CH₃)—C₂H₅,   —(CH₂)₃—C*H(CH₃)—C₂H₅ and
—C*H(CF₃)—CH₂—COO—C₂H₅.

17. The tetralin compound as claimed in claim 16, wherein Y¹ in the formula (I) is —O—CO or —COO—.

18. The tetralin compound is claimed in claim 16, wherein Z in the formula (I) is —O— or —O—CO—.

19. The tetralin compound as claimed in claim 16 wherein Z in the formula (I) is —O—.

20. The tetralin compound as claimed in claim 16 wherein the compound has the formula

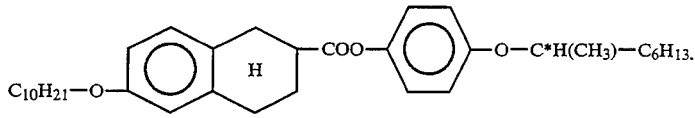

21. A tetralin compound represented by the following formula (I):

R—X—A¹—Y¹—A²—(Y²—A³)ₙ—Z—R*   (I)

wherein
R is an alkyl group of 3–20 carbon atoms,
X is —O—CO—, —O— or a single bond,
n is 1, one of A¹, A² and A³ is

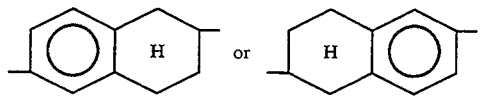

and the residual two of A¹, A², and A³ are 1,4-phenylene group,
Y¹ and Y² are each independently a group selected from the group consisting of —COO—, —O—CO—, —CH₂CH₂—, —CH₂O— and —OCH₂,
Z is —O—, —O—CO— or a single bond, and
R is a group selected from the group consisting of
—C*H(CF₃)—C₆H₁₃,   —C*H(CH₃)—C₆H₁₃,
—C*H(CH₃)—C₅H₁₁,   —C*H(C₂H₅)—C₅H₁₁,
—C*H(C₂H₅)—C₆H₁₃,   —CH₂—C*H(CH₃)—C₂H₅,   —(CH₂)₃—C₂H₅ and —C*H(CF₃)—CH₂—COO—C₂H₅.

22. The tetralin compound as claimed in claims 21, wherein Y¹ and Y² in the formula (I) are each independently —O—CO— or —COO—.

23. The tetralin compound as claimed in claim 21, wherein Z in the formula (I) is —O— or —O—CO—.

24. The tetralin compound as claimed in claim 21 wherein Z in the formula (I) is —O—.

25. The tetralin compound as claimed in claim 21 wherein the compound has the formula

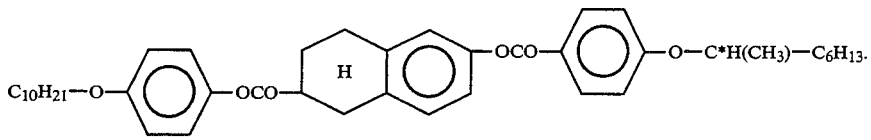

26. The tetralin compound as claimed in claim 21 wherein the compound has the formula

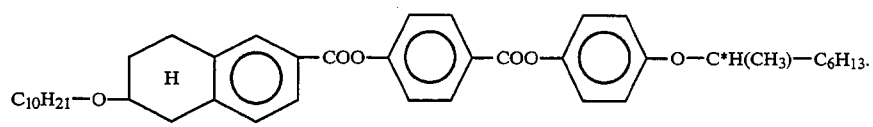
27. The tetralin compound as claimed in claim 21 wherein the compound has the formula
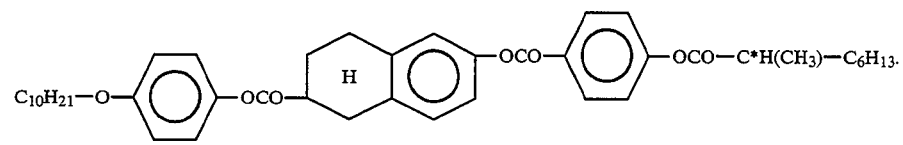
* * * * *